US012686674B2

(12) United States Patent
Liu et al.

(10) Patent No.: US 12,686,674 B2
(45) Date of Patent: Jul. 21, 2026

(54) CRYSTAL FORM OF COMPOUND REPRESENTED BY FORMULA I, AND PREPARATION THEREFOR AND APPLICATION THEREOF

(71) Applicant: Shanghai Zhimeng Biopharma, Inc., Shanghai (CN)

(72) Inventors: Gang Liu, Shanghai (CN); Bo Liang, Shanghai (CN); Zhaojian Jiang, Shanghai (CN); Huanming Chen, Shanghai (CN)

(73) Assignee: SHANGHAI ZHIMENG BIOPHARMA, INC., Shanghai (CN)

( * ) Notice: Subject to any disclaimer, the term of this patent is extended or adjusted under 35 U.S.C. 154(b) by 349 days.

(21) Appl. No.: 18/291,206

(22) PCT Filed: Jul. 22, 2022

(86) PCT No.: PCT/CN2022/107465

§ 371 (c)(1),
(2) Date: Jan. 22, 2024

(87) PCT Pub. No.: WO2023/001299

PCT Pub. Date: Jan. 26, 2023

(65) Prior Publication Data

US 2024/0368143 A1 Nov. 7, 2024

(30) Foreign Application Priority Data

Jul. 23, 2021 (CN) ......................... 202110839532.4

(51) Int. Cl.
*C07D 413/14* (2006.01)
*A61K 31/422* (2006.01)

(52) U.S. Cl.
CPC .......... *C07D 413/14* (2013.01); *A61K 31/422* (2013.01)

(58) Field of Classification Search
CPC ............................ C07D 413/14; A61K 31/422
See application file for complete search history.

(56) References Cited

U.S. PATENT DOCUMENTS 10,519,145 B2 * 12/2019 Chen .................... A61K 31/428
2019/0152963 A1 5/2019 Chen

FOREIGN PATENT DOCUMENTS

| | | | |
|---|---|---|---|
| CN | 114685473 | A | 7/2022 |
| WO | 2006033995 | A2 | 3/2006 |
| WO | 2007014023 | A1 | 2/2007 |
| WO | 2017173999 | A1 | 10/2017 |
| WO | 2018050110 | A1 | 3/2018 |

OTHER PUBLICATIONS

International Search Report and Written Opinion issued Oct. 18, 2022 in PCT/CN2022/107465 (Translation of ISR only).

* cited by examiner

*Primary Examiner* — Jeffrey S Lundgren
*Assistant Examiner* — Ibrahim D Bori
(74) *Attorney, Agent, or Firm* — Panitch Schwarze Belisario & Nadel LLP

(57) ABSTRACT

A crystal form of a compound represented by formula (I), and a preparation therefor and an application thereof are provided. Also disclosed are a variety of crystal forms of the compound represented by formula (I) (especially crystal form A). The crystal forms have the advantages of excellent stability, hygroscopicity and purity, etc., and has great significance for promoting later-stage drug development of the compound represented by formula (I).

Formula I

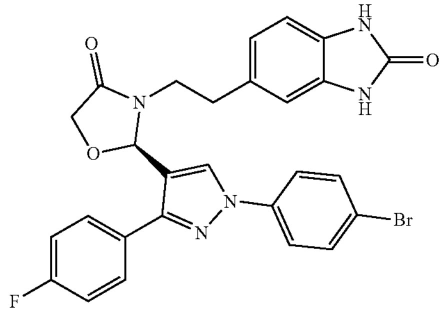

10 Claims, 15 Drawing Sheets

CRYSTAL FORM OF COMPOUND REPRESENTED BY FORMULA I, AND PREPARATION THEREFOR AND APPLICATION THEREOF

CROSS-REFERENCE TO RELATED APPLICATIONS

This application is a Section 371 of International Application No. PCT/CN2022/107465, filed Jul. 22, 2022, which was published in the Chinese language on Jan. 26, 2023 under International Publication No. WO 2023/001299 A1, which claims priority under 35 U.S.C. § 119(b) to Chinese Application No. 202110839532.4, filed Jul. 23, 2021, the disclosures of which are incorporated herein by reference in their entireties.

TECHNICAL FIELD

The present invention relates to the field of pharmaceutical chemistry, specifically to the crystal form of compound represented by formula I, preparation therefor, and application thereof.

BACKGROUND

The compounds represented by Formula I are nucleocapsid inhibitors of hepatitis B virus, developed by Shanghai Zhimeng biopharma, INC., which is a new type of novel drugs for hepatitis B in clinical trial stage. Currently marketed hepatitis B drugs can provide limited control of hepatitis B virus replication and delay the progression of cirrhosis, but can rarely cure chronic hepatitis B. The compound of formula I can improve the functional cure rate of chronic hepatitis B by inhibiting the formation of HBV nucleocapsid, and the results of preclinical studies have shown that it has excellent safety and efficacy.

Formula I

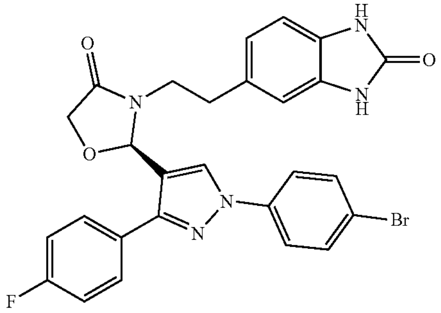

At present, there are no relevant reports on the crystal form of the above compound of formula I. In order to further optimize the druggability, safety, and efficacy of the compound, the present invention provides crystal forms of compound represented by formula I, preparation therefor, and application thereof.

SUMMARY OF THE INVENTION

The purpose of the invention is to provide crystal forms of compound of formula I with higher purity and better druggability, preparation therefor, and application thereof.

In the first aspect of the present invention, provided is a crystal form of a compound of Formula I:

Formula I

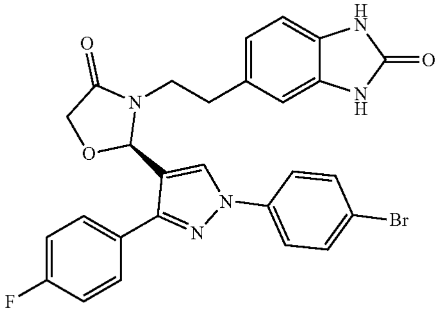

the crystal form is selected from the group consisting of:

1) crystal form A, wherein XRPD pattern of crystal form A has 3 or more 2θ values selected from the group consisting of: 24.052±0.2°, 17.967±0.2°, 17.352±0.2°, 12.414±0.2°, 24.399±0.2°, 26.578±0.2°, 11.764±0.2°, 19.16±0.2°, 16.423±0.2°, 22.67±0.2°, 18.269±0.2°, 32.318±0.2°, and 14.924±0.2°;
2) crystal form B, wherein XRPD pattern of crystal form B has 3 or more 2θ values selected from the group consisting of: 23.947±0.2°, 15.861±0.2°, 17.109±0.2°, 10.066±0.2°, 18.738±0.2°, 32.151±0.2°, 8.812±0.2°, and 4.645±0.2°;
3) crystal form D, wherein XRPD pattern of crystal form D has 3 or more 2θ values selected from the group consisting of: 24.324±0.2°, 26.505±0.2°, 21.737±0.2°, 17.783±0.2°, 16.018±0.2°, 19.383±0.2°, 27.214±0.2°, 13.234±0.2°, 13.446±0.2°, and 20.4±0.2°;
4) crystal form E, wherein XRPD pattern of crystal form E has 3 or more 2θ values selected from the group consisting of: 20.115±0.2°, 18.287±0.2°, 10.002±0.2°, 18.969±0.2°, 16.607±0.2°, 9.132±0.2°, 28.238±0.2°, 25.243±0.2°, 23.626±0.2°, 11.745±0.2°, 24.022±0.2°, and 12.538±0.2°;
5) crystal form F, wherein XRPD pattern of crystal form F has 3 or more 2θ values selected from the group consisting of: 11.228±0.2°, 18.503±0.2°, 21.753±0.2°, 16.737±0.2°, 20.331±0.2°, 19.21±0.2°, 10.153±0.2°, 22.536±0.2°, 16.05±0.2°, 10.749±0.2°, 20.687±0.2°, 11.851±0.2°, 12.692±0.2°, 9.246±0.2°, and 17.255±0.2°;
6) crystal form G, wherein XRPD pattern of crystal form G has 3 or more 2θ values selected from the group consisting of: 18.452±0.2°, 22.004±0.2°, 24.202±0.2°, 26.664±0.2°, 15.905±0.2°, 20.186±0.2°, 23.922±0.2°, 12.411±0.2°, 14.045±0.2°, 18.872±0.2°, 29.075±0.2°, 20.847±0.2°, 28.137±0.2°, 23.682±0.2°, 32.077±0.2°, and 30.333±0.2°.

In another preferred embodiment, the XRPD pattern of crystal form A has 6 or more 2θ values selected from the group consisting of: 24.052±0.2°, 17.967±0.2°, 17.352±0.2°, 12.414±0.2°, 24.399±0.2°, 26.578±0.2°, 11.764±0.2°, 19.16±0.2°, 16.423±0.2°, 22.67±0.2°, 18.269±0.2°, 32.318±0.2°, and 14.924±0.2°.

In another preferred embodiment, the XRPD pattern of crystal form A has 10 or more 2θ values selected from the group consisting of: 24.052±0.2°, 17.967±0.2°, 17.352±0.2°, 12.414±0.2°, 24.399±0.2°, 26.578±0.2°, 11.764±0.2°, 19.16±0.2°, 16.423±0.2°, 22.67±0.2°, 18.269±0.2°, 32.318±0.2°, 14.924±0.2°, 18.54±0.2°, 25.687±0.2°, 27.68±0.2°, 9.091±0.2°, 21.275±0.2°, 28.291±0.2°, 27.397±0.2°, 35.136±0.2°, 33.792±0.2°, and 23.702±0.2°.

In another preferred embodiment, the XRPD pattern of crystal form A has 10 or more 2θ values selected from the group consisting of: 24.052±0.2°, 17.967±0.2°, 17.352±0.2°, 12.414±0.2°, 24.399±0.2°, 26.578±0.2°, 11.764±0.2°, 19.16±0.2°, 16.423±0.2°, 22.67±0.2°, 18.269±0.2°, 32.318±0.2°, 14.924±0.2°, 18.54±0.2°, 25.687±0.2°, 27.68±0.2°, 9.091±0.2°, 21.275±0.2°, 28.291±0.2°, 27.397±0.2°, 35.136±0.2°, 33.792±0.2°, 23.702±0.2°, 23.19±0.2°, 27.974±0.2° 31.068±0.2°, 29.139±0.2°, 31.535±0.2°, 34.775±0.2°, 19.912±0.2°, 36.58±0.2°, 30.187±0.2°, 33.534±0.2°, 16.939±0.2°, 16.688±0.2°, 38.988±0.2°, 22.276±0.2°, 34.067±0.2°, 34.54±0.2°, 35.551±0.2°, 8.783±0.2°, 28.632±0.2°, 37.874±0.2°, 30.526±0.2°, and 33.098±0.2°.

In another preferred embodiment, the XRPD pattern of crystal form A has the following 2θ values: 24.052±0.2°, 17.967±0.2°, 17.352±0.2°, 12.414±0.2°, 24.399±0.2°, 26.578±0.2°, 11.764±0.2°, 19.16±0.2°, 16.423±0.2°, 22.67±0.2°, 18.269±0.2°, 32.318±0.2°, 14.924±0.2°, 18.54±0.2°, 25.687±0.2°, 27.68±0.2°, 9.091±0.2°, 21.275±0.2°, 28.291±0.2°, 27.397±0.2°, 35.136±0.2°, 33.792±0.2°, 23.702±0.2°, 23.19±0.2°, 27.974±0.2° 31.068±0.2°, 29.139±0.2°, 31.535±0.2°, 34.775±0.2°, 19.912±0.2°, 36.58±0.2°, 30.187±0.2°, 33.534±0.2°, 16.939±0.2°, 16.688±0.2°, 38.988±0.2°, 22.276±0.2°, 34.067±0.2°, 34.54±0.2°, 35.551±0.2°, 8.783±0.2°, 28.632±0.2°, 37.874±0.2°, 30.526±0.2°, and 33.098±0.2°.

In another preferred embodiment, the XRPD pattern of crystal form A has the following 2θ values: 24.052, 17.967, 17.352, 12.414, 24.399, 26.578, 11.764, 19.16, 16.423, 22.67, 18.269, 32.318, 14.924, 18.54, 25.687, 27.68, 9.091, 21.275, 28.291, 27.397, 35.136, 33.792, 23.702, 23.19, 27.974, 31.068, 29.139, 31.535, 34.775, 19.912, 36.58, 30.187, 33.534, 16.939, 16.688, 38.988, 22.276, 34.067, 34.54 35.551, 8.783, 28.632, 37.874, 30.526, and 33.098.

In another preferred embodiment, the XRPD pattern of crystal form A is substantially as shown in FIG. 1.

In another preferred embodiment, the crystal form A is an anhydrous crystal form.

In another preferred embodiment, water content of crystal form A is ≤0.5%; preferably ≤0.2%, more preferably ≤0.1%.

In another preferred embodiment, the crystal form A has an endothermic peak at 244-248° C.

In another preferred embodiment, the crystal form A has a TGA/DSC pattern substantially as shown in FIG. 3.

In another preferred embodiment, the purity of crystal form A is ≥99.5%, preferably ≥99.7%, and more preferably ≥99.9%.

In another preferred embodiment, the XRPD pattern of crystal form B has 6 or more 2θ values selected from the group consisting of: 23.947±0.2°, 15.861±0.2°, 17.109±0.2°, 10.066±0.2°, 18.738±0.2°, 32.151±0.2°, 8.812±0.2°, and 4.645±0.2°.

In another preferred embodiment, the XRPD pattern of crystal form B has the following 2θ values: 23.947±0.2°, 15.861±0.2°, 17.109±0.2°, 10.066±0.2°, 18.738±0.2°, 32.151±0.2°, 8.812±0.2°, and 4.645±0.2°.

In another preferred embodiment, the XRPD pattern of crystal form B has the following 2θ values: 23.947, 15.861, 17.109, 10.066, 18.738, 32.151, 8.812, and 4.645.

In another preferred embodiment, the XRPD pattern of crystal form B is substantially as shown in FIG. 4.

In another preferred embodiment, weight loss of crystal form B is 4.7-8% before 210° C.

In another preferred embodiment, the crystal form B has endothermic peaks at 150-165° C. and 245-250° C.; and/or crystal form B has an exothermic peak at 182-192° C.

In another preferred embodiment, the crystal form B has a TGA/DSC pattern substantially as shown in FIG. 5.

In another preferred embodiment, the crystal form B is a solvate.

In another preferred embodiment, the XRPD pattern of crystal form D has 6 or more 2θ values selected from the group consisting of: 24.324±0.2°, 26.505±0.2°, 21.737±0.2°, 17.783±0.2°, 16.018±0.2°, 19.383±0.2°, 27.214±0.2°, 13.234±0.2°, 13.446±0.2°, and 20.4±0.2°.

In another preferred embodiment, the XRPD pattern of crystal form D has 10 or more 2θ values selected from the group consisting of: 24.324±0.2°, 26.505±0.2°, 21.737±0.2°, 17.783±0.2°, 16.018±0.2°, 19.383±0.2°, 27.214±0.2°, 13.234±0.2°, 13.446±0.2°, 20.4±0.2°, 14.049±0.2°, 14.874±0.2°, 24.833±0.2°, 16.882±0.2°, 23.296±0.2°, 28.146±0.2°, 19.888±0.2°, 16.419±0.2°, and 32.839±0.2°.

In another preferred embodiment, the XRPD pattern of crystal form D has 10 or more 2θ values selected from the group consisting of: 24.324±0.2°, 26.505±0.2°, 21.737±0.2°, 17.783±0.2°, 16.018±0.2°, 19.383±0.2°, 27.214±0.2°, 13.234±0.2°, 13.446±0.2°, 20.4±0.2°, 14.049±0.2°, 14.874±0.2°, 24.833±0.2°, 16.882±0.2°, 23.296±0.2°, 28.146±0.2°, 19.888±0.2°, 16.419±0.2°, 32.839±0.2°, 29.031±0.2°, 22.664±0.2°, 10.817±0.2°, 30.426±0.2°, 34.905±0.2° 36.698±0.2°, 29.52±0.2°, 9.564±0.2°, 25.225±0.2°, 30.041±0.2°, 32.097±0.2°, 35.215±0.2°, 37.977±0.2°, 39.383±0.2°, 36.192±0.2°, 33.768±0.2°, 39.129±0.2°, and 12.522±0.2°.

In another preferred embodiment, the XRPD pattern of crystal form D has the following 2θ values: 24.324±0.2°, 26.505±0.2°, 21.737±0.2°, 17.783±0.2°, 16.018±0.2°, 19.383±0.2°, 27.214±0.2°, 13.234±0.2°, 13.446±0.2°, 20.4±0.2°, 14.049±0.2°, 14.874±0.2°, 24.833±0.2°, 16.882±0.2°, 23.296±0.2°, 28.146±0.2°, 19.888±0.2°, 16.419±0.2°, 32.839±0.2°, 29.031±0.2°, 22.664±0.2°, 10.817±0.2°, 30.426±0.2°, 34.905±0.2° 36.698±0.2°, 29.52±0.2°, 9.564±0.2°, 25.225±0.2°, 30.041±0.2°, 32.097±0.2°, 35.215±0.2°, 37.977±0.2°, 39.383±0.2°, 36.192±0.2°, 33.768±0.2°, 39.129±0.2°, and 12.522±0.2°.

In another preferred embodiment, the XRPD pattern of crystal form D has the following 2θ values: 24.324, 26.505, 21.737, 17.783, 16.018, 19.383, 27.214, 13.234, 13.446, 20.4, 14.049, 14.874, 24.833, 16.882, 23.296, 28.146, 19.888, 16.419, 32.839, 29.031, 22.664, 10.817, 30.426, 34.905, 36.698, 29.52, 9.564, 25.225, 30.041, 32.097, 35.215, 37.977, 39.383, 36.192, 33.768, 39.129, and 12.522.

In another preferred embodiment, the XRPD pattern of crystal form D is substantially as shown in FIG. 10.

In another preferred embodiment, the crystal form D has a weight lose of 16.81% before 180° C.

In another preferred embodiment, the crystal form D has an endothermic peak at 111-115° C.

In another preferred embodiment, the crystal form D has an endothermic peak at 243-250° C.

In another preferred embodiment, the crystal form D has a TGA/DSC pattern substantially as shown in FIG. 11.

In another preferred embodiment, the crystal form D is a solvate.

In another preferred embodiment, the XRPD pattern of crystal form E has 6 or more 2θ values selected from the group consisting of: 20.115±0.2°, 18.287±0.2°, 10.002±0.2°, 18.969±0.2°, 16.607±0.2°, 9.132±0.2°, 28.238±0.2°, 25.243±0.2°, 23.626±0.2°, 11.745±0.2°, 24.022±0.2°, and 12.538±0.2°.

In another preferred embodiment, the XRPD pattern of crystal form E has 10 or more 2θ values selected from the group consisting of: 20.115±0.2°, 18.287±0.2°, 10.002±0.2°, 18.969±0.2°, 16.607±0.2°, 9.132±0.2°, 28.238±0.2°, 25.243±0.2°, 23.626±0.2°, 11.745±0.2°, 24.022±0.2°, 12.538±0.2°, 21.701±0.2°, 14.006±0.2°, 30.392±0.2°, 29.151±0.2°, 27.509±0.2°, 16.057±0.2°, 21.085±0.2°, 19.39±0.2°, 22.872±0.2°, 22.327±0.2°, 6.984±0.2°, 26.431±0.2° 12.824±0.2°, 26.802±0.2°, 15.066±0.2°, 33.301±0.2°, 38.968±0.2°, 10.597±0.2°, 31.95±0.2°, 32.261±0.2°, 30.738±0.2°, 33.682±0.2°, 15.721±0.2°, 37.098±0.2°, and 25.834±0.2°.

In another preferred embodiment, the XRPD pattern of crystal form E has the following 2θ values: 20.115±0.2°, 18.287±0.2°, 10.002±0.2°, 18.969±0.2°, 16.607±0.2°, 9.132±0.2°, 28.238±0.2°, 25.243±0.2°, 23.626±0.2°, 11.745±0.2°, 24.022±0.2°, 12.538±0.2°, 21.701±0.2°, 14.006±0.2°, 30.392±0.2°, 29.151±0.2°, 27.509±0.2°, 16.057±0.2°, 21.085±0.2°, 19.39±0.2°, 22.872±0.2°, 22.327±0.2°, 6.984±0.2°, 26.431±0.2° 12.824±0.2°, 26.802±0.2°, 15.066±0.2°, 33.301±0.2°, 38.968±0.2°, 10.597±0.2°, 31.95±0.2°, 32.261±0.2°, 30.738±0.2°, 33.682±0.2°, 15.721±0.2°, 37.098±0.2°, and 25.834±0.2°.

In another preferred embodiment, the XRPD pattern of the crystal form E has the following 2θ values: 20.115, 18.287, 10.002, 18.969, 16.607, 9.132, 28.238, 25.243, 23.626, 11.745, 24.022, 12.538, 21.701, 14.006, 30.392, 29.151, 27.509, 16.057, 21.085, 19.39, 22.872, 22.327, 6.984, 26.431, 12.824, 26.802, 15.066, 33.301, 38.968, 10.597, 31.95, 32.261, 30.738, 33.682, 15.721, 37.098, and 25.834.

In another preferred embodiment, the XRPD pattern of crystal form E is substantially as shown in FIG. 14.

In another preferred embodiment, the crystal form E has a weight lose of 4.69% before 210° C.

In another preferred embodiment, the crystal form E has endothermic peaks at 110-130° C. and 140-155° C.

In another preferred embodiment, the crystal form E has an exothermic peak at 170-188° C.

In another preferred embodiment, the crystal form E has an endothermic peak at 240-250° C.

In another preferred embodiment, the crystal form E has a TGA/DSC pattern substantially as shown in FIG. 15.

In another preferred embodiment, the XRPD pattern of crystal form F has 6 or more 2θ values selected from the group consisting of: 11.228±0.2°, 18.503±0.2°, 21.753±0.2°, 16.737±0.2°, 20.331±0.2°, 19.21±0.2°, 10.153±0.2°, 22.536±0.2°, 16.05±0.2°, 10.749±0.2°, 20.687±0.2°, 11.851±0.2°, 12.692±0.2°, 9.246±0.2°, and 17.255±0.2°.

In another preferred embodiment, the XRPD pattern of crystal form F has 10 or more 2θ values selected from the group consisting of: 11.228±0.2°, 18.503±0.2°, 21.753±0.2°, 16.737±0.2°, 20.331±0.2°, 19.21±0.2°, 10.153±0.2°, 22.536±0.2°, 16.05±0.2°, 10.749±0.2°, 20.687±0.2°, 11.851±0.2°, 12.692±0.2°, 9.246±0.2°, and 17.255±0.2°.

In another preferred embodiment, the XRPD pattern of crystal form F has 10 or more 2θ values selected from the group consisting of: 11.228±0.2°, 18.503±0.2°, 21.753±0.2°, 16.737±0.2°, 20.331±0.2°, 19.21±0.2°, 10.153±0.2°, 22.536±0.2°, 16.05±0.2°, 10.749±0.2°, 20.687±0.2°, 11.851±0.2°, 12.692±0.2°, 9.246±0.2°, 17.255±0.2°, 15.057±0.2°, 23.846±0.2°, 14.252±0.2°, 7.498±0.2°, 5.193±0.2°, 13.804±0.2°, and 25.474±0.2°.

In another preferred embodiment, the XRPD pattern of crystal form F has the following 2θ values: 11.228±0.2°, 18.503±0.2°, 21.753±0.2°, 16.737±0.2°, 20.331±0.2°, 19.21±0.2°, 10.153±0.2°, 22.536±0.2°, 16.05±0.2°, 10.749±0.2°, 20.687±0.2°, 11.851±0.2°, 12.692±0.2°, 9.246±0.2°, 17.255±0.2°, 15.057±0.2°, 23.846±0.2°, 14.252±0.2°, 7.498±0.2°, 5.193±0.2°, 13.804±0.2°, and 25.474±0.2°.

In another preferred embodiment, the XRPD pattern of crystal form F has the following 2θ values: 11.228, 18.503, 21.753, 16.737, 20.331, 19.21, 10.153, 22.536, 16.05, 10.749, 20.687, 11.851, 12.692, 9.246, 17.255, 15.057, 23.846, 14.252, 7.498, 5.193, 13.804, and 25.474.

In another preferred embodiment, the crystal form F has a weight loss of 2.695% before 210° C.

In another preferred embodiment, the XRPD pattern of crystal form G has 6 or more 2θ values selected from the group consisting of: 18.452±0.2°, 22.004±0.2°, 24.202±0.2°, 26.664±0.2°, 15.905±0.2°, 20.186±0.2°, 23.922±0.2°, 12.411±0.2°, 14.045±0.2°, 18.872±0.2°, 29.075±0.2°, 20.847±0.2°, 28.137±0.2°, 23.682±0.2°, 32.077±0.2°, and 30.333±0.2°.

In another preferred embodiment, the XRPD pattern of crystal form G has 10 or more 2θ values selected from the group consisting of: 18.452±0.2°, 22.004±0.2°, 24.202±0.2°, 26.664±0.2°, 15.905±0.2°, 20.186±0.2°, 23.922±0.2°, 12.411±0.2°, 14.045±0.2°, 18.872±0.2°, 29.075±0.2°, 20.847±0.2°, 28.137±0.2°, 23.682±0.2°, 32.077±0.2°, and 30.333±0.2°.

In another preferred embodiment, the XRPD pattern of crystal form G has 10 or more 2θ values selected from the group consisting of: 18.452±0.2°, 22.004±0.2°, 24.202±0.2°, 26.664±0.2°, 15.905±0.2°, 20.186±0.2°, 23.922±0.2°, 12.411±0.2°, 14.045±0.2°, 18.872±0.2°, 29.075±0.2°, 20.847±0.2°, 28.137±0.2°, 23.682±0.2°, 32.077±0.2°, 30.333±0.2°, 13.815±0.2°, 24.935±0.2°, 27.652±0.2°, 21.088±0.2°, 26.177±0.2°, 17.534±0.2°, 30.889±0.2°, 35.293±0.2°, 33.922±0.2°, 29.875±0.2°, 16.334±0.2°, 38.674±0.2°, 38.538±0.2°, 14.587±0.2°, 7.041±0.2°, 10.559±0.2°, and 5.489±0.2°.

In another preferred embodiment, the XRPD pattern of crystal form G has the following 2θ values: 18.452±0.2°, 22.004±0.2°, 24.202±0.2°, 26.664±0.2°, 15.905±0.2°, 20.186±0.2°, 23.922±0.2°, 12.411±0.2°, 14.045±0.2°, 18.872±0.2°, 29.075±0.2°, 20.847±0.2°, 28.137±0.2°, 23.682±0.2°, 32.077±0.2°, 30.333±0.2°, 13.815±0.2°, 24.935±0.2°, 27.652±0.2°, 21.088±0.2°, 26.177±0.2°, 17.534±0.2°, 30.889±0.2°, 35.293±0.2°, 33.922±0.2°, 29.875±0.2°, 16.334±0.2°, 38.674±0.2°, 38.538±0.2°, 14.587±0.2°, 7.041±0.2°, 10.559±0.2°, and 5.489±0.2°.

In another preferred embodiment, the XRPD pattern of crystal form G has the following 2θ values: 18.452, 22.004, 24.202, 26.664, 15.905, 20.186, 23.922, 12.411, 14.045, 18.872, 29.075, 20.847, 28.137, 23.682, 32.077, 30.333, 13.815, 24.935, 27.652, 21.088, 26.177, 17.534, 30.889, 35.293, 33.922, 29.875, 16.334, 38.674, 38.538, 14.587, 7.041, 10.559, and 5.489.

In another preferred embodiment, the XRPD pattern of crystal form G is substantially as shown in FIG. 19.

In another preferred embodiment, the crystal form G has endothermic peaks at 218-222° C. and 245-250° C.; and/or the crystal form G has a sharp exothermic peak at 220-224° C.

In another preferred embodiment, the crystal form G has a TGA/DSC pattern substantially as shown in FIG. 20.

In another preferred embodiment, the crystal form G is an anhydrous crystal form.

In the second aspect of the present invention, provided is a pharmaceutical composition, comprising:

1) the crystal form as described in the first aspect of the present invention; and 2) pharmaceutically acceptable carriers or excipients.

In the third aspect of the present invention, provided is a use of the crystal form as described in the first aspect of the present invention in the preparation of drugs against hepatitis B virus.

In another preferred embodiment, the drug is used for treating hepatitis B virus infection in mammals.

It should be understood that, within the scope of the present invention, each of the above technical features of the present invention and each of the technical features specifically described in the following (such as the embodiments) can be combined with each other to constitute a new or preferred technical solution. Due to space limitations, it will not be repeated herein.

EMBODIMENTS FOR CARRYING OUT THE INVENTION

Figure 1:
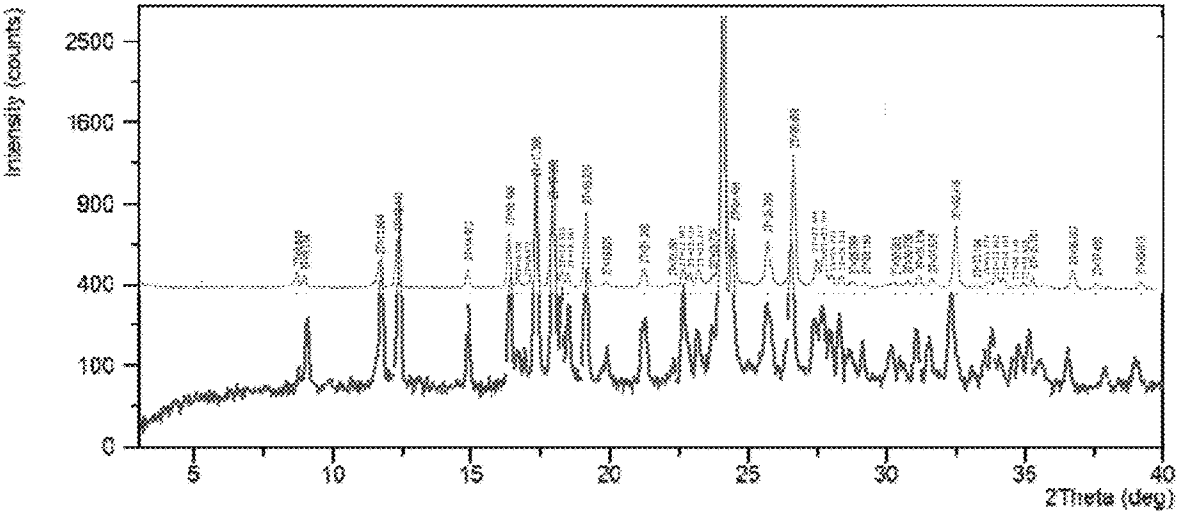
FIG. 1 shows the XRPD pattern of crystal form A obtained in Example 1.

After long-term and in-depth research, the inventor has obtained a crystal form of the compound of formula I with higher purity and better druggability through extensive screening and process optimization. The inventor has completed the present invention on this basis.

As used herein, the term "n or more 2θ values selected from the group consisting of" refers to any positive integer including n and any positive integer greater than n (e.g., n, n+1, . . . ), where the upper limit Nup is the number of all 2θ peaks in the group. For example, "1 or more" not only includes each positive integers such as 1, 2, 3, 4, 5, 6, 7, 8, 9, 10, 11, 12, 13, 14, 15, 16, 17, 18, 19, 20, 21, . . . upper limit Nup, but also includes ranges such as "2 or more", "3 or more", "4 or more", "5 or more", "6 or more", "7 or more", "8 or more", "9 or more", 10 or more. For example, "3 or more" not only includes each positive integers such as 3, 4, 5, 6, 7, 8, 9, 10, 11, 12, 13, 14, 15, 16, 17, 18, 19, 20, 21, . . . upper limit Nup, but also includes ranges such as "4 or more", "5 or more", "6 or more", "7 or more", "8 or more", "9 or more", "10 or more", etc.

The present invention has the following main advantages over the prior art:

(1) Compared to the compound disclosed in WO2017173999 A1, the crystal form of the present invention is the most stable crystal form; meanwhile, the crystallization and purification methods disclosed in the present invention are less costly and more conducive to the operational process of scaling up production;

(2) Compared to WO2017173999 A1, the present invention obtains a crystal form with high purity, high yield, and significantly lower impurity content through optimized processes;

(3) Compared to WO2017173999 A1, the amorphous product obtained therefrom has a risk of precipitation pf crystals during placement and has poor solid-state stability. The crystal form obtained in the present invention has higher solid-state stability and is more conducive to long-term storage. The data also shows that the crystal form is chemically stable with good performance, and there are fewer impurities generated during the process with statistical significance, resulting in a longer storage period of the API.

The present invention was further described hereafter in combination with specific embodiments. It should be understood that these examples are only used to illustrate the and not to limit the scope of the invention. The experimental methods without specific conditions in the following examples generally follow the conventional conditions or the conditions suggested by the manufacturer. Unless otherwise stated, percentages and parts are calculated by weight.

Unless otherwise defined, all professional and scientific terms used in the text have the same meanings as those familiar to those skilled in the art. In addition, any methods and materials similar or equal to the recorded content can be applied to the methods of the present invention. The preferred embodiments and materials described herein are for exemplary purposes only.

General Test Method:

X-Ray Powder Diffraction (XRPD)

X-ray powder diffraction data of the samples were collected under ambient conditions using a Bruker D2 model X-ray powder diffractometer with an X-ray emitter power of 300 W. The sample stage has no background signal, with a step rate of 0.15 s/step, a total of 1837 steps, and a step size of 2θ=0.02°, a voltage of 30 kV, and a current of 10 mA. The X-ray tube uses Cu target (Kα) with a Kα2/Kα1 intensity ratio of 0.50 (1.54439 Å/1.5406 Å).

High Performance Liquid Chromatography (HPLC)

Sample purity and solubility data were collected using an Agilent model 1260 high-performance liquid chromatograph (equipped with DAD detector). Test method was shown in table A.

TABLE A

Summary of HPLC methods for testing purity and solubility of samples

| Project | Parameters |
|---|---|
| instrument | Agilent model 1200 high-performance liquid chromatograph or other equivalent systems |
| Chromatographic column | Waters XBridge Phenyl 250 × 4.6 mm, 5 μm (PN: 186003353) or other equivalent chromatographic column |
| Mobile Phase: | A: $H_2O$<br>B: ACN/MeOH (80:20, v/v) |
| Detector | UV, 278 nm |
| Temperature of chromatographic column | 30° C. |
| Flow rate | 1.0 mL/min |
| Injection volume | 10 μL |

TABLE A-continued

Summary of HPLC methods for testing purity and solubility of samples

| Project | Parameters | | |
|---|---|---|---|
| Needle washing solvent | ACN/$H_2O$ (9:1, v/v) | | |
| Diluent | ACN/$H_2O$ (9:1, v/v) | | |
| | time(min) | % A | % B |
| elution procedure for Sample purity test | 0.0 | 55 | 45 |
| | 3.0 | 55 | 45 |
| | 20.0 | 40 | 60 |
| | 35.0 | 10 | 90 |
| | 50.0 | 10 | 90 |
| | 50.1 | 55 | 45 |
| | 57.0 | 55 | 45 |

Polarization Microscope (PLM)

Micrographs of samples were collected using the BX53M polarization microscope produced by Olympus at room temperature.

Thermogravimetric Analysis (TGA)

Thermogravimetric data of samples were collected using the TA Discovery series thermogravimetric analyzer (TGA). Several milligrams of the sample was placed in a Tzero aluminum plate, and heated from room temperature to 400° C. under $N_2$ protection, with a $N_2$ flow rate of 25 mL/min and a heating rate of 10° C./min.

Differential Scanning Calorimeter (DSC)

Thermal data of samples were collected using a TA Discovery series differential scanning calorimeter (DSC). Several milligrams of the sample was weighted and placed in a Tzero aluminum and sealed with a Tzero sealing cover, then heated under $N_2$ protection, with a $N_2$ flow rate of 50 mL/min and a heating rate of 10° C./min.

Dynamic Vapor Phase Adsorption System (DVS)

Hygroscopicity data of samples were collected using an ADVENTURE series dynamic vapor phase adsorption system (DVS) under $N_2$ protection. Sample dosage ~30 mg. The testing method for anhydrous crystal form is as follows:

1) Relative humidity increase process: 0% RH to 90% RH at a rate of 10% RH/stage; 90% RH to 95% RH at a rate of 5% RH/stage;
2) Relative humidity reduction process: 95% RH to 90% RH at a rate of 5% RH/stage; 90% RH to 5% RH at a rate of 10% RH/stage.

H Nuclear Magnetic Resonance Spectroscopy (H-NMR)

H nuclear magnetic resonance spectrum data of samples were collected using Agilent VNMR 400MR. Several milligrams of the sample was taken and dissolved in DMSO-d6 reagent, and detected by the instrument.

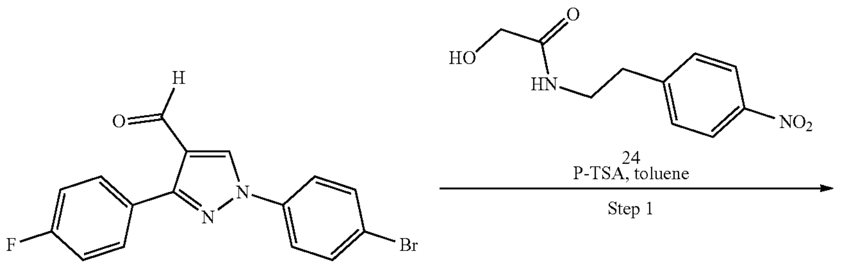

24

31

-continued
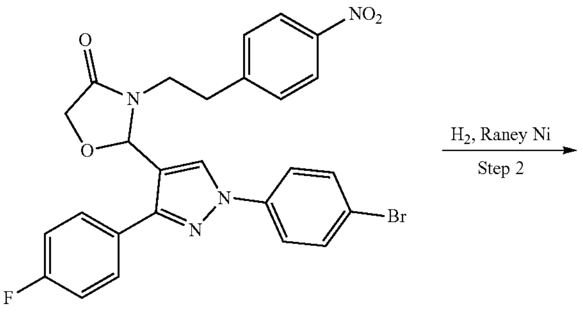
32
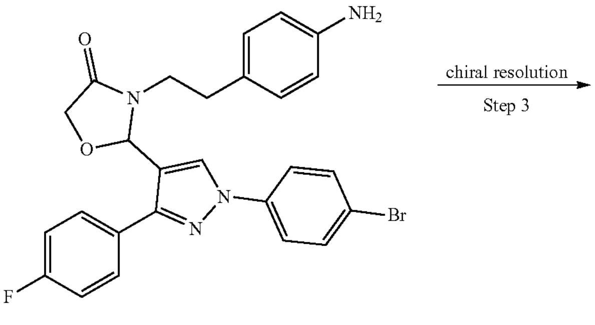
33
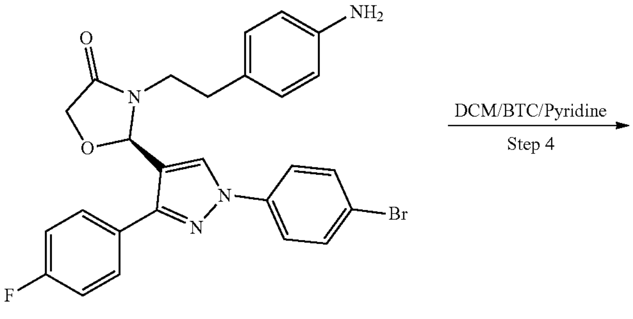
34
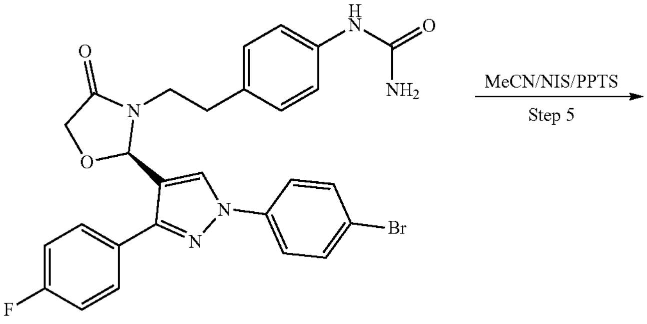
17

-continued

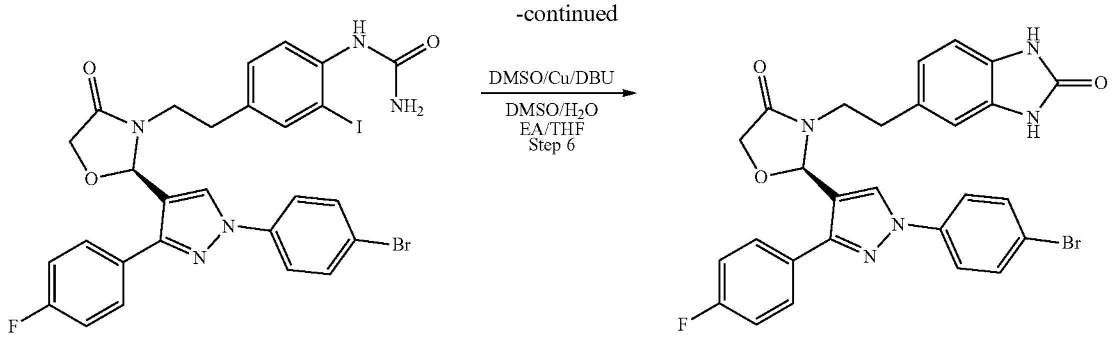

9 4

PREPARATION EXAMPLE OF RAW MATERIAL

Example A-1 Synthesis of Compound 32

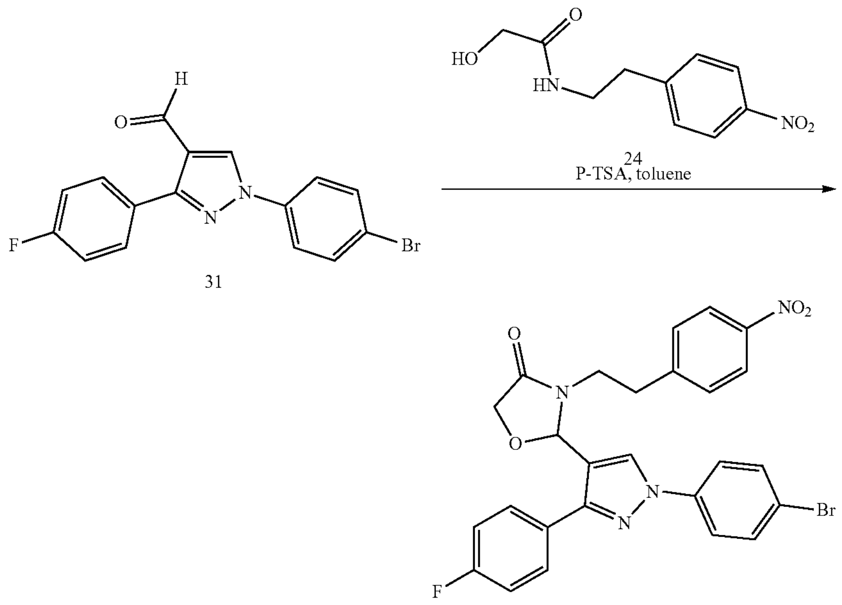

31

32

At room temperature, to a reactor was added sequentially toluene (303 kg), compound 31 (35 kg), and p-toluene sulfonic acid (7 kg), heated up to 105-115° C., and stirred to separate water for 1 hour. The reaction was cooled down to 60-80° C., and the reactor was added with compound 24 (28.33 kg), heated up to 110-120° C., and refluxed to separate water for 12 hours. The reaction was cooled down to 78-80° C., added with additional p-toluene sulfonic acid (180 g) and compound 24 (505 g), and continued heating and refluxing for 7-8 hours to separate water. HPLC control showed complete conversion of compound 31; the reaction system was cooled down to 50-55° C., added with methanol (35.4 kg) and stirred for 2 hours. After cooling and filtration, the resulting filter cake was rinsed with a small amount of toluene/methanol solution. The filter cake was dried to give 40.5 kg of compound 32 with a yield of 72.5% and HPLC purity of 98%. MS: $[M+H]^+$=551.4/553.4

Example A-2 Synthesis of Compound 33

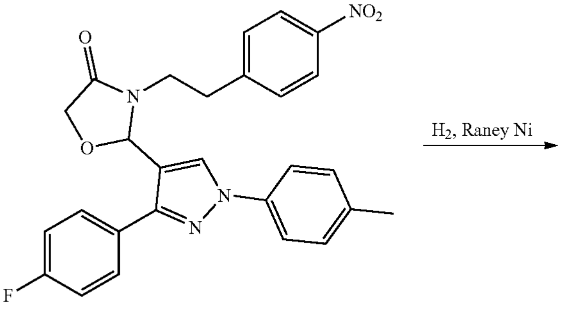

32

-continued

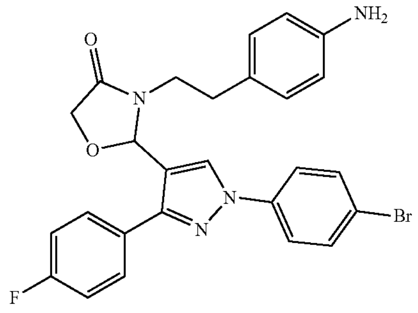

33

At room temperature, to a reaction bottle were added ethyl acetate (8 L, 44.8V), compound 32 (178.3 g, 1.0 eq.), triethylamine (80 mL, 0.45V) and Raney nickel (48 g, 27%). The reaction system was replaced three times with hydrogen and reacted at room temperature for 8 hours. HPLC control showed complete conversion of compound 32. After filtration, the filtrate was concentrated to give 160.4 g of compound 33, with a yield of 95.1% and HPLC purity of 98.2%. MS: $[M+H]^+=521.5/523.5$ Example A-3 Separation of Compound 33

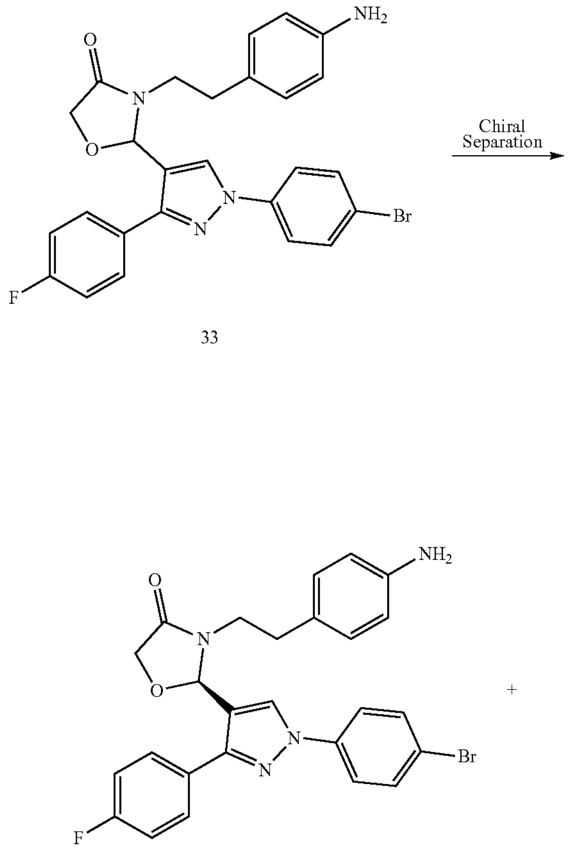

33

34

-continued

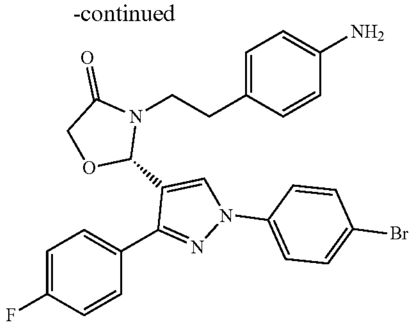

34-S 5 g of racemic compound 33 was taken and subjected to chiral separation using a chiral chromatographic column, with methanol as the main mobile phase. 1.3 g of compound 34 (ee>99%) and 1.78 g of compound 34-S were obtained through chiral separation.

Example A-4 Synthesis of Compound 17

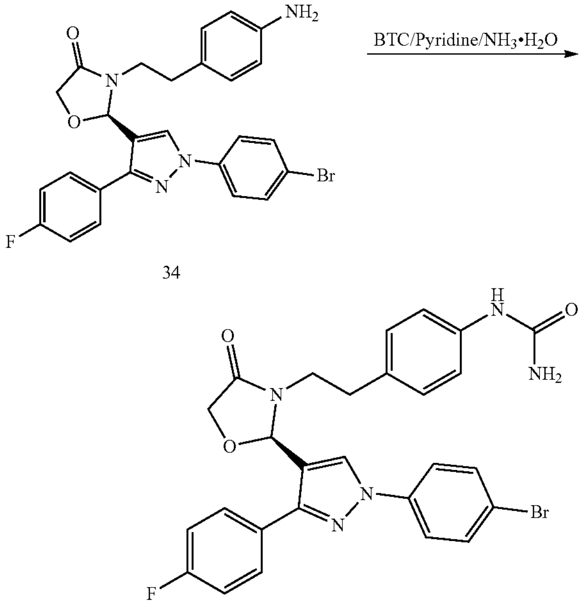

34

17 to the reactor was added dichloromethane (6 L) and cooled down to about −10° C. Triphosgene (BTC) (170.75 g, 0.58 mol) was added. A solution of compound 34 (600 g, 1.15 mol) in dichloromethane (4.8 L) was added slowly and dropwise to the above dichloromethane solution of triphosgene. Stirred for 30 min. Keeping the temperature below −5° C., a solution of pyridine (273.07 g, 3.45 mol) in dichloromethane (1.2 L) was added. After addition, the reaction was kept stirring for more than 20 minutes. Keeping the temperature below −5° C., ammonia (0.9 L) was added dropwise and the reaction was continued for no less than 30 minutes.

After HPLC monitoring showed completion of reaction, the reaction was washed twice with water and then concentrated. The obtained product was dissolved in ethyl acetate and then added with n-hexane for beating. The filter cake was collected and dried to give 590 g of compound 17 with a yield of 90.86% and purity of 98.45%. MS: $[M+H]^+$ =563.01/565.02

Example A-5 Synthesis of Compound 9

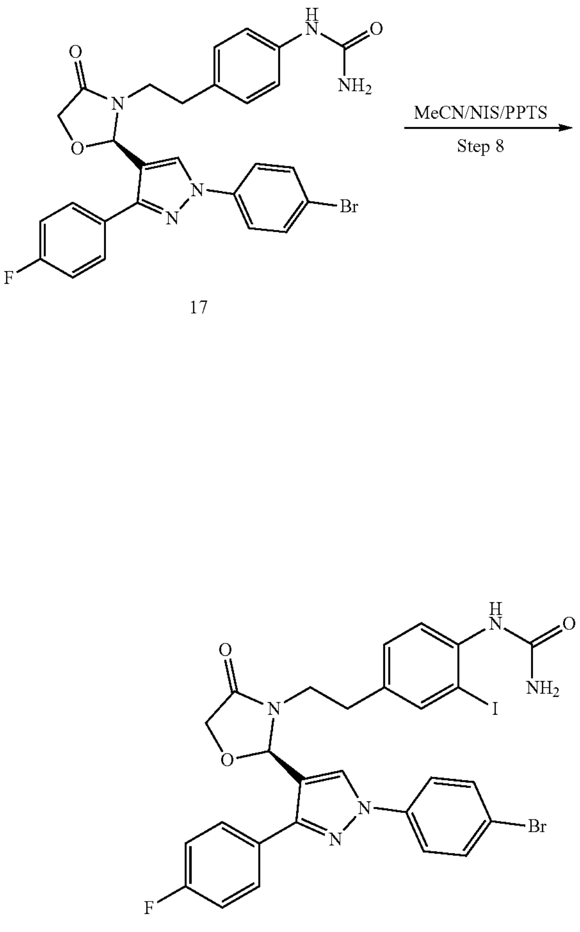

17

9

To a solution of compound 17 (190 g, 0.337 mol) in acetonitrile (1.3 L) was added PPTS (Pyridine p-toluene sulfonate) (42.3 g, 0.168 mol) and NIS (N-iodosuccinimide) (90.88 g, 0.4 mol). A large amount of solid precipitated after overnight reaction at 56° C. After passing the HPLC test, the reaction was cooled down to 20-30° C. and washed with 5% sodium sulfite solution. The solid was collected by suction filtration and the resulting solid was washed with MTBE (methyl tert-butyl ether), and dried to give 202 g of compound 9 with a yield of 86.9% and purity of 98.75%. MS: $[M+H]^+$=689.84/691.84

For more details on the preparation of the compounds, see the following application filed on the same day as the present invention:

Name of the invention: PREPARATION METHOD FOR HEPATITIS B VIRUS NUCLEOCAPSID INHIBITOR Date of application: Jul. 23, 2021

Applicant: SHANGHAI ZHIMENG BIOPHARMA, INC.

PREPARATION EXAMPLES OF CRYSTAL FORMS

Example 1 Preparation and Characterization of Crystal Form A

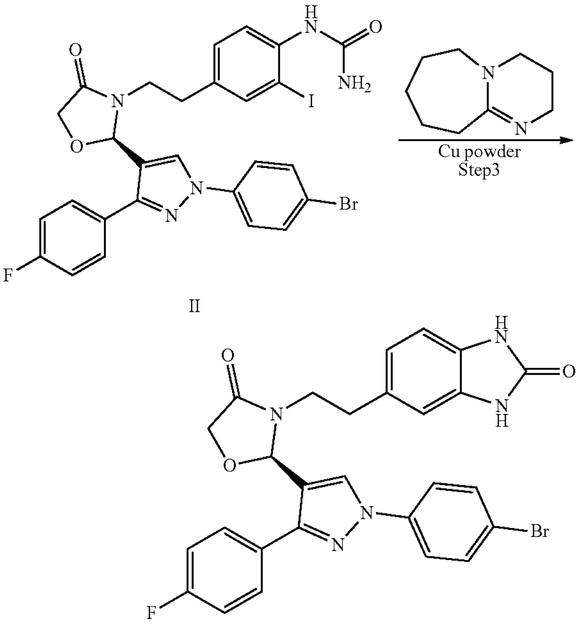

II

I 25.760 kg of DMSO (dimethyl sulfoxide) was added to the reactor under nitrogen protection, and started stirring. 2.9 kg of Compound II was added to the reactor under 40° C. with stirring. 0.74 kg of DBU was added to the same reactor. 0.27 kg of copper powder was added to the same reactor. After addition, the reaction was heated up to 70° C. and reacted for more than 8 hours. After detecting the complete conversion of compound II, the temperature was lowered to under 30° C. and 0.3 kg of activated carbon was added to the reactor. After stirring for 30 min, the reaction solution was filtered to remove activated carbon and copper powder. The filter cake was washed with a small amount of dimethyl sulfoxide. The filtrates were combined and added with 32 kg of 10% aqueous acetic acid solution. After addition, the reaction was kept under 40° C. and stirred for 1 hour then filtered. The filter cake was washed with a small amount of potable water and collected. The resulting filter cake was beat with 66 kg of a solvent mixture of ethyl acetate:tetrahydrofuran (4:1) and then filtered, and the filter cake was washed with a small amount of tetrahydrofuran. The filtrate was transferred to a reactor. The resulting solution was washed with 16.4 kg of 10% aqueous acetic acid solution, 15 kg of 1% aqueous potassium carbonate solution and 15.6 kg of 5% aqueous sodium chloride solution, respectively. The organic phase was dried with anhydrous sodium sulfate and filtered. The filtrate was collected and concentrated under reduced pressure to remove the organic solvent until no solvent flowed out. 6.8 kg of acetone was weighed and evaporated until no solvent flowed out. 4.6 kg of acetone was weighed and added to the residue and heated to reflux for 1 hour. The temperature was cooled to 5-10° C. The reaction solution was stirred for 1 hour then filtrated. The filter cake was washed with a small amount of acetone. The resulting solid wet product was dried to ≤1% moisture. 1.655 Kg of crude compound I was obtained as greyish yellow to light yellow solid powder with a yield of 70.3% and a purity of 99.68%.

6.2 Kg of acetic acid and 1.655 Kg of crude compound I were added to the reaction flask and heated to 80±5° C. until the solution turned clear. After filtering at no less than 50° C. and then cooled down to 25° C., the reaction solution was filtered and the filter cake was washed with a small amount of water. The resulting solid wet product was dried to give 1.538 Kg of Compound I (elaboration product I) as yellowish to off-white solid powder with a yield of 93.1% and a purity of 99.9%.

To a reactor was added 2.432 Kg of acetone and 1.538 Kg of Compound I (elaboration product I). The reaction was warmed to reflux and continued stirring at reflux for more than 1 hour, then cooled down and filtered, the filter cake was washed with a small amount of acetone. The resulting solid wet product was dried to obtain 1.458 Kg of product crystal form A of compound I as off-white solid powder with a yield of 94.8%, and a purity of 99.90%.

Figure 31:
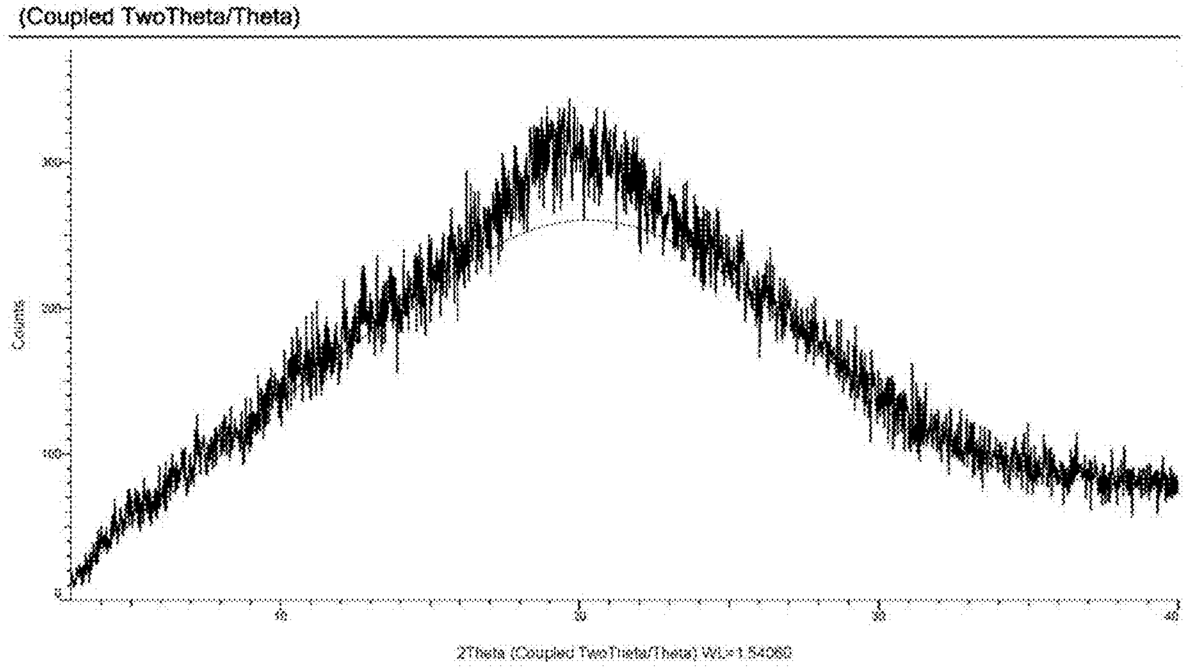
FIG. 31 shows the XRPD pattern of compound I obtained from Example 3 of WO2017173999 A1.

Results:

1) In terms of solid-state properties, after repeated, the white solid of compound I obtained by chiral separation in Example 3 of WO2017173999 A1 is amorphous (the XRPD results of which can be found in FIG. 31 of the present invention).

Specifically, the white solid of compound I prepared in Example 3 of WO2017173999 A1 is amorphous with poor solid stability and a single stable crystal form does not obtained. API prepared by this method have uncertainty in solid-state stability, and there is also a risk of further precipitation of crystal when storage for a long period of time. There is uncertainty in the solubility and bioavailability of the corresponding samples, resulting in poor druggability.

2) In terms of chemical purity, the product purity reported in Example 3 of WO2017173999 A1 is only 98.47%. The difference in purity was large compared to the 99.90% purity of the product obtained in Example 1 of the present invention. Given that in the synthesis of Example 3 of WO2017173999 A1, the intermediates in the last three steps, 3-(4-acetylamino-3-nitrophenylethyl)-2-(3-(4-fluorophenyl)-1-(4-bromophenyl)-1H-pyrazole-4-yl) oxazolidin-4-one, 3-(4-amino-3-nitrophenylethyl)-2-(1-(4-bromophenyl)-3-(4-fluorophenyl)-1H-pyrazole-4-yl) oxazolidin-4-one, 2-(1-(4-bromophenyl)-3-(4-fluorophenyl)-1H-pyrazole-4-yl)-3-(3,4-diaminophenethyl) oxazolidin-4-one have been shown to be positive in AMES experiments, indicating potential risks. The residue of these three impurities in API will seriously affect the quality of the API. The crystal form A disclosed in the present invention and preparation therefor and purification process effectively avoids the use of related intermediates, with a purity of generally above 99.5%, and more preferably 99.90%, which effectively reduces the residues of various harmful impurities in the API.

Table M-1 showed the test results of crystal form A obtained in Example 1.

TABLE M-1

| | Batch number: R191043 |
|---|---|
| appearance | Off-white powder |
| Moisture (KF) | 0.09% |
| Residue on ignition (ROI) | 0.02% |
| Specific rotation$[\alpha]_D^{20}$ (c = 0.25, tetrahydrofuran) | +50.4° |
| Total impurities | 0.10% |
| Enantiomer(HPLC) | Not detected |
| Content (HPLC)(calculated by anhydrous substance | 99.3% |

TABLE M-2

Influencing factor test results of Crystal form A of Example 1 (High Temperature, High Humidity)
Batch number: R191042 Batch size: 1.206 kg Specification: API (bare sample)

| Test period: Aug. 9th, 2019 to Sep. 9th, 2019 | | | Batch number: R191042 | | | | | | |
|---|---|---|---|---|---|---|---|---|---|
| | | | High temperature (60° C.) | | | | High humidity (25° C., 90% ± 5%) | | |
| Serial Number | Test item | Quality standard | Day 0 | Day 5 | Day 10 | Day 30 | Day 5 | Day 10 | Day 30 |
| 1 | appearance | White, off-white to light yellow powder | Off-white powder | Off-white powder | Off-white powder | Off-white powder | Off-white powder | Off-white powder | Off-white powder |
| 2 | Moisture (KF) | No more than 1.0% | 0.11% | 0.09% | 0.09% | 0.09% | 0.21% | 0.23% | 0.10% |
| 3 | | | | Substances of interest(HPLC) | | | | | |
| | Compound II | No more than 0.2% | Not detected | Not detected | Not detected | Not detected | Not detected | Not detected | Not detected |
| | Other single impurity | No more than 0.3% | RRT~1.10:0.14%<br>RRT~1.23:0.03%<br>RRT~1.44:0.03%<br>RRT~1.53:0.03%<br>RRT~1.8 | RRT~1.10:0.13%<br>RRT~1.24:0.04%<br>RRT~1.48:0.03%<br>RRT~1.59:0.03%<br>RRT~1.9 | RRT~1.10:0.14%<br>RRT~1.24:0.03%<br>RRT~1.46:0.03%<br>RRT~1.56:0.03%<br>RRT~1.9 | RRT~1.10:0.14%<br>RRT~1.24:0.03%<br>RRT~1.48:0.03%<br>RRT~1.58:0.03%<br>RRT~1.9 | RRT~1.10:0.14%<br>RRT~1.24:0.04%<br>RRT~1.48:0.03%<br>RRT~1.59:0.03%<br>RRT~1.9 | RRT~1.10:0.13%<br>RRT~1.24:0.03%<br>RRT~1.46:0.03%<br>RRT~1.56:0.03%<br>RRT~1.8 | RRT~1.10:0.15%<br>RRT~1.24:0.03%<br>RRT~1.48:0.03%<br>RRT~1.59:0.03%<br>RRT~1.9 |

TABLE M-2-continued

Influencing factor test results of Crystal form A of Example 1 (High Temperature, High Humidity)
Batch number: R191042 Batch size: 1.206 kg Specification: API (bare sample)

| Test period: Aug. 9th, 2019 to Sep. 9th, 2019 | | | Batch number: R191042 | | | | | | |
|---|---|---|---|---|---|---|---|---|---|
| | | | High temperature (60° C.) | | | | High humidity (25° C., 90% ± 5%) | | |
| Serial Number | Test item | Quality standard | Day 0 | Day 5 | Day 10 | Day 30 | Day 5 | Day 10 | Day 30 |
| | | | 7:0.03% | 2:0.03% RRT~1.9 7:0.03% | 3:0.03% | 2:0.03% RRT~1.9 7:0.03% | 2:0.03% RRT~1.9 7:0.03% | 8:0.03% RRT~1.9 3:0.03% | 2:0.03% RRT~1.9 7:0.03% |
| | Total impurities | No more than 1.5% | 0.26% | 0.29% | 0.26% | 0.29% | 0.30% | 0.28% | 0.30% |
| 4 | Enantiomer (HPLC) | No more than 1.0% | Not detected | Not detected | Not detected | Not detected | Not detected | Not detected | Not detected |
| 5 | Content (HPLC, calculated by anhydrous substance) | 98.0%~102.0% | 99.2% | 99.1% | 99.8% | 100.9% | 99.4% | 99.7% | 101.3% |

TABLE M-3

Influencing factor test results of crystal form A of example 1 (High Temperature, High Humidity, Light Conditions)
Batch number: R191042 Batch dose: 1.206 kg Specification: API (bare sample)

| | | | Batch number: R191042 | | | | | | |
|---|---|---|---|---|---|---|---|---|---|
| Test period: Aug. 9th, 2019 to Sep. 9th, 2019 | | | High temperature and humidity (60° C., 75% ± 5%) | | | | Light exposure(25° C., 4500 Lx ± 500 Lx, NUV 0.9 w/m$^2$), bare sample | | |
| Serial Number | Test item | Quality standard | Day 0 | Day 5 | Day 10 | Day 30 | Day 5 | Day 10 | Day 30 |
| 1 | appearance | White, off-white to light yellow powder | Off-white powder | Off-white powder | Off-white powder | Off-white powder | Off-white powder | Off-white powder | Off-white powder |
| 2 | Moisture (KF) | No more than 1.0% | 0.11% | 0.12% | 0.14% | 0.14% | 0.10% | 0.10% | 0.10% |
| 3 | Substances of interest(HPLC) | | | | | | | | |
| | Compound II | No more than 0.2% | Not detected | Not detected | Not detected | Not detected | Not detected | Not detected | Not detected |
| | Other single impurity | No more than 0.3% | RRT~1.1 0:0.13% RRT~1.2 4:0.03% RRT~1.4 8:0.03% RRT~1.5 8:0.03% RRT~1.9 7:0.03% | RRT~1.1 0:0.14% RRT~1.2 4:0.03% RRT~1.4 6:0.03% RRT~1.5 6:0.03% RRT~1.8 8:0.03% RRT~1.9 3:0.03% | RRT~1.1 0:0.14% RRT~1.2 4:0.03% RRT~1.4 8:0.03% RRT~1.5 9:0.03% RRT~1.9 7:0.03% | RRT~1.1 0:0.14% RRT~1.2 4:0.03% RRT~1.4 8:0.03% RRT~1.5 8:0.03% RRT~1.9 6:0.03% | RRT~1.1 0:0.14% RRT~1.2 4:0.03% RRT~1.4 6:0.03% RRT~1.5 6:0.03% RRT~1.9 3:0.03% | RRT~1.1 0:0.14% RRT~1.2 4:0.03% RRT~1.4 8:0.03% RRT~1.5 9:0.03% RRT~1.9 7:0.03% | RRT~1.1 0:0.13% RRT~1.2 4:0.03% RRT~1.4 8:0.03% RRT~1.5 8:0.03% RRT~1.9 7:0.03% |
| | Total impurities | No more than 1.5% | 0.25% | 0.29% | 0.26% | 0.26% | 0.26% | 0.26% | 0.25% |
| 4 | Enantiomer (HPLC) | No more than 1.0% | Not detected | Not detected | Not detected | Not detected | Not detected | Not detected | Not detected |
| 5 | Content (HPLC, calculated by anhydrous substance) | 98.0%~102.0% | 99.8% | 99.6% | 101.3% | 99.3% | 99.6% | 100.7% | 99.8% |

Based on the comparative data from the above influencing factor tests, it can be seen that the starting purity of crystal form A (99.75%) is higher when compared to the 98.47% purity of the Compound I sample obtained in Example 3 of WO2017173999 A1. Meanwhile, under high temperature and high humidity conditions, crystal form A exhibited good chemical stability and good druggability.

FIG. 1 shows the XRPD pattern of crystal form A obtained in Example 1.

Table 1-1 listed summary of XRPD data of the crystal form A, with an error range of 2θ values being ±0.2°.

TABLE 1-1

Summary of XRPD data ofcrystal form A

| No. | 2θ(°) | Intensity |
|---|---|---|
| 1 | 8.783 | 1.90% |
| 2 | 9.091 | 7.50% |
| 3 | 11.764 | 18.10% |
| 4 | 12.414 | 31.50% |
| 5 | 14.924 | 10.20% |
| 6 | 16.423 | 13.10% |
| 7 | 16.688 | 2.70% |
| 8 | 16.939 | 2.80% |
| 9 | 17.352 | 41.50% |
| 10 | 17.967 | 41.90% |
| 11 | 18.269 | 11.50% |
| 12 | 18.54 | 8.70% |
| 13 | 19.16 | 15.30% |
| 14 | 19.912 | 3.60% |
| 15 | 21.275 | 7.10% |
| 16 | 22.276 | 2.40% |
| 17 | 22.67 | 12.30% |
| 18 | 23.19 | 4.50% |
| 19 | 23.702 | 5.10% |
| 20 | 24.052 | 100.0% |
| 21 | 24.399 | 21.80% |
| 22 | 25.687 | 8.30% |
| 23 | 26.578 | 20.20% |
| 24 | 27.397 | 5.90% |
| 25 | 27.68 | 8.20% |
| 26 | 27.974 | 4.50% |
| 27 | 28.291 | 6.20% |
| 28 | 28.632 | 1.90% |
| 29 | 29.139 | 3.80% |
| 30 | 30.187 | 3.40% |
| 31 | 30.526 | 1.20% |
| 32 | 31.068 | 4.30% |
| 33 | 31.535 | 3.80% |
| 34 | 32.318 | 11.00% |
| 35 | 33.098 | 1.00% |
| 36 | 33.534 | 2.90% |
| 37 | 33.792 | 5.20% |
| 38 | 34.067 | 2.10% |
| 39 | 34.54 | 2.00% |
| 40 | 34.775 | 3.80% |
| 41 | 35.136 | 5.40% |
| 42 | 35.551 | 2.00% |
| 43 | 36.58 | 3.50% |
| 44 | 37.874 | 1.70% |
| 45 | 38.988 | 2.50% |

Figure 2:
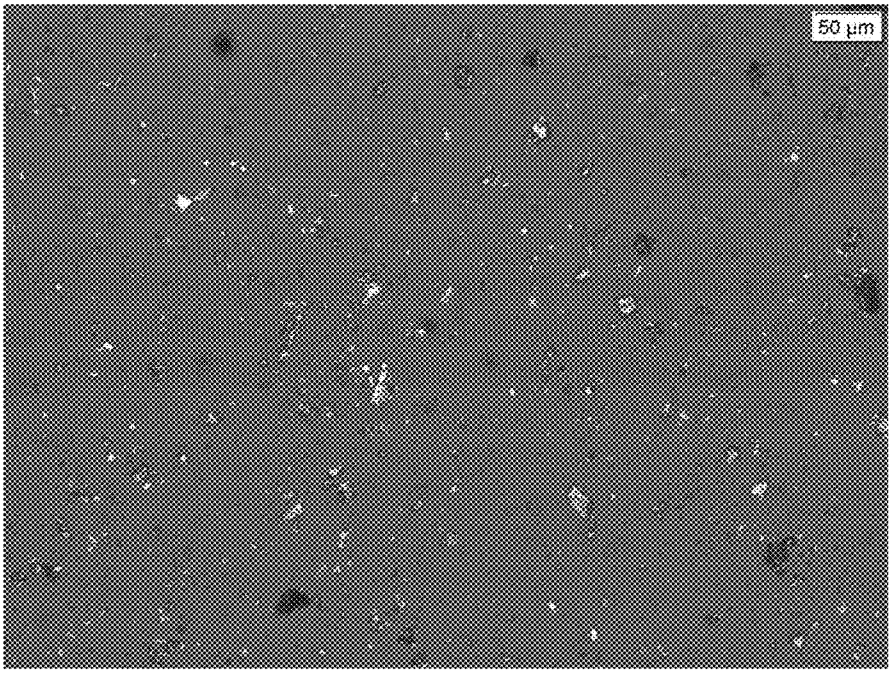
FIG. 2 shows the PLM diagram of crystal form A (200×).

FIG. 2 shows the PLM diagram of crystal form A(200×).

From FIG. 2, it can be seen that crystal form A is tiny granulars.

Figure 3:
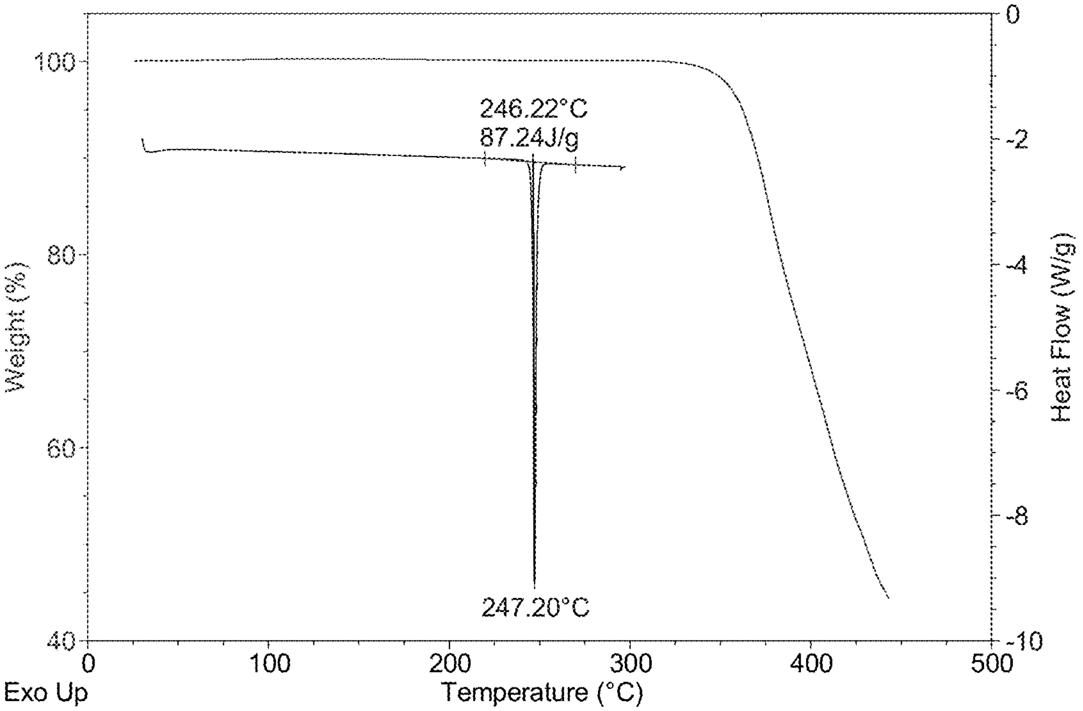
FIG. 3 shows the TGA/DSC pattern of crystal form A.

FIG. 3 shows the TGA/DSC pattern of crystal form A.

From FIG. 3, it can be seen that the sample showed almost no weight loss before decomposition, with a sharp melting peak at 246.2° C. (onset temperature).

The above results indicated that crystal form A is anhydrous crystal form.

Example 2 Discussion on Screening Results of More Crystal Forms

Screening of More Crystal Forms

Based on the relevant properties of compound I, considering conditions such as solvent type and temperature, a total of 65 crystal forms screening experiments were set up. The method include anti-solvent addition, gas-solid diffusion, gas-liquid diffusion, slow volatilization, polymer induction, stirring at room temperature/50° C., and slow cooling. Specific description of the method can be found in the following text.

It should be understood that compound I used in the crystal form screening below was compound I prepared by the preparation method shown in the present invention.

Anti-Solvent Addition Method

~15 mg of Compound I sample was weighed and added to the ortho-solvent listed in Table 2 below, and stirred at room temperature to obtain clear stock solution. The stock solution was divided into 20 mL of glass bottles and 0.2~0.5 mL of corresponding antisolvent was added to the glass bottle under magnetic stirring until solid appears or the total solvent volume reaches 15.0 mL. The results (table 1) showed that through the anti-solvent addition method, crystal form A, crystal form B, a mixture of crystal form A and B, and a mixture of crystal forms E and A were obtained.

TABLE 1 results of anti-solvent addition

| Test number | Ortho-solvent | Anti-solvent | The crystal form obtained |
|---|---|---|---|
| D220-PS-03-A1# | MeOH | IPAc | Crystal form B |
| D220-PS-03-A2 | | $H_2O$ | Crystal form A |
| D220-PS-03-A3 | Acetone | n-Heptane | Crystal form A |
| D220-PS-03-A4 | | $H_2O$ | Crystal form A |
| D220-PS-03-A5# | | CPME | Crystal form A + B |
| D220-PS-03-A6 | THF | Toluene | Crystal form B |
| D220-PS-03-A7 | | n-Heptane | Crystal form A |
| D220-PS-03-A8# | | MIBK | Crystal form A |
| D220-PS-03-A9 | 1,4-Dioxane | $H_2O$ | Crystal form A |
| D220-PS-03-A10# | | EtOAc | Crystal form A |
| D220-PS-03-A11# | DMSO | Toluene | Crystal form A |
| D220-PS-03-A12 | | $H_2O$ | Crystal form E + A |
| D220-PS-03-A13# | DMF | MTBE | Crystal form A |
| D220-PS-03-A14# | | ACN | Crystal form A |

#Becoming clear after the addition of anti-solvent at 5° C./−20° C., solid were obtained by volatilisation at room temperature

Gas-Solid Diffusion Method 12 mg of crystal form A sample of compound I was weighed in a 4 mL glass vial and the vial was placed in a 20 mL glass vial containing 3 mL of volatile solvent. The 20 mL glass vial was capped tightly and left at room temperature for about two weeks and the resulting solids were characterized by XRPD. The results showed that (table 2) crystal forms A and D were obtained by gas-solid diffusion method.

TABLE 2

Results of Gas-solid diffusion

| Test number | Solvent | The crystal form obtained |
|---|---|---|
| D220-PS-04-A1 | EtOH | Crystal form A |
| D220-PS-04-A2 | MEK | Crystal form A |
| D220-PS-04-A3 | 2-MeTHF | Crystal form A |
| D220-PS-04-A4 | EtOAc | Crystal form A |
| D220-PS-04-A5 | $CHCl_3$ | Crystal form A |
| D220-PS-04-A6 | DMSO | Crystal form A |
| D220-PS-04-A7 | DMF | Crystal form A |
| D220-PS-04-A8 | $CH_3COOH$ | Crystal form D |

Gas-Liquid Diffusion Method

~15 mg of compound I sample was weighed in a 4 mL glass bottle, the corresponding solvent in Table 4 was added to dissolve the sample, then placed in a 20 mL glass bottle containing 4 mL of anti-solvent. The 20 mL glass vial was capped tightly and left at room temperature until solid precipitated. The resulting solid was subjected to XRPD characterization. The results indicated that (table 3) crystal forms A and B were obtained by gas-liquid diffusion method.

TABLE 3

Results of gas-liquid diffusion

| Test number | Solvent | Anti-solvent | The crystal form obtained |
|---|---|---|---|
| D220-PS-05-A1 | 1,4-Dioxane | n-Heptane | Crystal form B |
| D220-PS-05-A2* | DMSO | MTBE | Crystal form A |
| D220-PS-05-A3 | | $H_2O$ | Crystal form A |
| D220-PS-05-A4* | DMF | IPAc | Crystal form A |
| D220-PS-05-A5* | | DCM | Crystal form A |

*After 21 days, the sample was clear and the solid was obtained by volatilization at room temperature.

Method of Slow Volatilization at Room Temperature

~15 mg of Compound I sample was weighed in a 4 mL glass vial and the corresponding solvent in Table 5 below was added to dissolve it, then sealed with sealing film and punctured 4 to 6 pinholes and volatilized slowly at room temperature. The final solid obtained was subjected to XRPD characterization. The results showed that (table 4), three crystal forms were obtained by method of slow volatilization at room temperature, namely crystal forms A/B/E.

TABLE 4

Results of slow volatilization at room temperature

| Test number | Solvent | The crystal form obtained |
|---|---|---|
| D220-PS-06-A1 | MeOH | Crystal form E |
| D220-PS-06-A2 | Acetone | Crystal form A |
| D220-PS-06-A3 | 2-MeTHF | Crystal form B |

Polymer Induction Method 8-15 mg of crystal form A sample of compound I was weighed in a 4 mL glass vial and the corresponding solvent was added to dissolve it. If not turning clear, the suspension was subjected to membrane filtration (nylon membrane, membrane pore size 0.22 μm). 1-2 mg of polymer (PVC/PVP 1:1, w/w) was added to the filtrate, then the 4 mL glass vial was sealed with sealing film and punctured 4 to 6 pinholes and volatilized slowly at room temperature. The final solid obtained was subjected to XRPD characterization. The results indicated that (table 5), only crystal form A was obtained by polymer induction method.

TABLE 5

Results of polymer induction

| Test number | Solvent | The crystal form obtained |
|---|---|---|
| D220-PS-07-A1 | EtOH | Crystal form A |
| D220-PS-07-A2 | MEK | Crystal form A |
| D220-PS-07-A3 | THF | Crystal form A |

Method of Stirring at Room Temperature

~15 mg of crystal form A sample of compound I was weighed in an HPLC vial, 0.4 mL of the corresponding solvent was added, and magnetic stirred at room temperature to obtain a suspension. The solid was separated about a week later and subjected to XRPD characterization. The results showed that (table 6), two crystal forms were obtained by method of stirring at room temperature, namely crystal forms A and D.

TABLE 6

Results of stirring at room temperature

| Test number | Solvent(v:v) | The crystal form obtained |
|---|---|---|
| D220-PS-08-A1 | MeOH | Crystal form A |
| D220-PS-08-A2 | EtOH | Crystal form A |
| D220-PS-08-A3 | MEK | Crystal form A |
| D220-PS-08-A4 | EtOAc | Crystal form A |
| D220-PS-08-A5 | THF/n-Heptane (1:3) | Crystal form A |
| D220-PS-08-A6 | 1,4-Dioxane/$H_2O$ (1:1) | Crystal form A |
| D220-PS-08-A7 | MTBE | Crystal form A |
| D220-PS-08-A8 | ACN | Crystal form A |
| D220-PS-08-A9 | DCM | Crystal form A |
| D220-PS-08-A10 | Toluene | Crystal form A |
| D220-PS-08-A11 | Acetone | Crystal form A |
| D220-PS-08-A12 | Acetone/$H_2O$ (984:16, v/v, $a_w$ = 0.2) | Crystal form A |
| D220-PS-08-A13 | Acetone/$H_2O$ (948:52, v/v, $a_w$ = 0.4) | Crystal form A |
| D220-PS-08-A14 | Acetone/$H_2O$ (857:143, v/v, $a_w$ = 0.6) | Crystal form A |
| D220-PS-08-A15 | Acetone/$H_2O$ (604:396, v/v, $a_w$ = 0.8) | Crystal form A |
| D220-PS-08-A16 | $H_2O$ | Crystal form A |
| D220-PS-08-A17 | $CH_3COOH$ | Crystal form D |

Method of Stirring at 50° C.

~15 mg of crystal form A sample of compound I was weighed in an HPLC vial, 0.4 mL of the corresponding solvent was added, and magnetic stirred at 50° C. to obtain a suspension. 3 days later, the solid in the suspension was subjected to XRPD characterization. The results indicated that (table 7) only crystal form A was obtained by method of stirring at 50° C.

TABLE 7

Results of stirring at 50° C.

| Test number | Solvent(v:v) | The crystal form obtained |
|---|---|---|
| D220-PS-09-A1 | MeOH/$H_2O$ (1:1) | Crystal form A |
| D220-PS-09-A2 | IPA | Crystal form A |
| D220-PS-09-A3 | MIBK | Crystal form A |
| D220-PS-09-A4 | IPAc | Crystal form A |
| D220-PS-09-A5 | 2-MeTHF/n-Heptane (1:3) | Crystal form A |
| D220-PS-09-A6 | CPME | Crystal form A |
| D220-PS-09-A7 | ACN | Crystal form A |
| D220-PS-09-A8 | $CHCl_3$ | Crystal form A |
| D220-PS-09-A9 | Acetone/$H_2O$ (1:3) | Crystal form A |
| D220-PS-09-A10 | Toluene | Crystal form A |

Method of Slow Cooling

~20 mg of crystal form A sample of compound I was weighed in a 4 mL glass vial, 0.6~0.8 mL of corresponding solvent was added, and magnetic stirred at 50° C. for 3 hours to obtain a suspension. The suspension was subjected to membrane filtration (nylon membrane, membrane pore size 0.22 μm). the filtrate was slowly cooled from 50° C. to 5° C. with a cooling rate of 0.1° C./min. The sample was stored at 5° C. for 2 days and then transferred to −20° C. to induce crystallization. The sample was stored at −20° C. for 5 days and then evaporated at room temperature. The final solid obtained was subjected to XRPD characterization. The results indicated that (table 8) crystal forms A, B, and E were obtained through method of slow cooling.

TABLE 8

| Results of slow cooling experiment | | |
|---|---|---|
| Test number | Solvent(v:v) | The crystal form obtained |
| D220-PS-10-A1 | IPA | Crystal form A |
| D220-PS-10-A2 | EtOAc/1,4-Dioxane (1:1) | Crystal form B |
| D220-PS-10-A3 | ACN | Crystal form A |

TABLE 8-continued

| Results of slow cooling experiment | | |
|---|---|---|
| Test number | Solvent(v:v) | The crystal form obtained |
| D220-PS-10-A4 | $CHCl_3$/Acetone (1:1) | Crystal form A |
| D220-PS-10-A5 | MEK | Crystal form E |

All samples are clear after slowly cooling to −20° C. and solids were obtained by volatilisation at room temperature. See table B for solvent names in English and Chinese.

TABLE B

| Comparison Table of solvent names in Chinese and English | | | |
|---|---|---|---|
| English | Chinese | English | Chinese |
| MeOH | Methanol | MTBE | Methyl tert-butyl ether |
| EtOH | Ethanol | CPME | Cyclopentyl methyl ether |
| IPA | Isopropanol | $CHCl_3$ | Trichloromethane |
| $CH_3COOH$ | Acetic acid | DCM | Dichloromethane |
| Acetone | Acetone | n-Heptane | n-Heptane |
| MEK | Butanone | Toluene | Toluene |
| MIBK | Methyl isobutyl ketone | DMSO | Dimethyl sulfoxide |
| EtOAc | Ethyl acetate | DMF | N,N-dimethylformamide |
| IPAc | Isopropyl acetate | ACN | Acetonitrile |
| THF | tetrahydrofuran | 1,4-Dioxane | 1,4-Dioxane |
| 2-MeTHF | 2-Methyltetrahydrofuran | $H_2O$ | $H_2O$ |

The results showed that compound I has six crystal forms, including four found in crystal form screening experiments (named crystal form A/B/D/E) and two found in subsequent crystal form identification (named crystal form F/G). Among them, three are anhydrous crystal form (crystal form A/F/G), one is hydrate (crystal form E), and two are solvate (crystal form B/D). Summary of screening results was shown in FIG. 10. The characterization data of six crystal forms were summarized in FIG. 11, and the XRPD comparison pattern was shown in FIG. 22.

TABLE 10

| Summary of screening results of crystal forms | | |
|---|---|---|
| Method of crystallization | Number of experiments | Crystal form |
| Anti-solvent addition | 14 | Crystal form A/B/A + E |
| Gas-solid diffusion | 8 | Crystal form A/D |
| Gas-liquid diffusion | 5 | Crystal form A/B |
| Slow volatilization | 3 | Crystal form A/B/E |
| Polymer induction | 3 | Crystal form A |
| Stirring at room temperature | 17 | Crystal form A/D |
| Stirring at 50° C. | 10 | Crystal form A |
| Slow cooling | 5 | Crystal form A/B/E |
| Total | 65 | Crystal form A/B/D/E |

TABLE 11

Summary of characterization data for six crystal forms of compound of formula I

| Type of crystal form | Crystal form (Batch number) | Preparation condition | TGA weight loss (%, [° C.]) | DSC signal (Starting temperature, ° C.) | Crystal form after heating ([° C.]) |
|---|---|---|---|---|---|
| Anhydrous crystal form | Crystal form A (01-A) | Starting sample | Almost no weight loss before decomposition | 246.2 | NA |
| | Crystal form F[@] (06-A1 AFT130) | Heating crystal form E to 130° C. | — | — | Crystal form E [room temperature] |
| | Crystal form G (11-A1 AFT210) | Heating crystal form E to 210° C. | Almost no weight loss before decomposition | 220.3[#]/222.0[#]*/246.1 | Crystal form A[230][&] |
| Hydrate | Crystal form E (06-A1) | volatilization at room temperature MeOH | 4.7% [210] H-NMR without methanol | 115.1/145.6/172.9*/ 220.3/222.3*/245.4 | Crystal form F[130] Weak crystallinity [170] Crystal form A + G[210] Crystal form A[230] |
| Solvate (isomorphism) | Crystal form B (03-A6) | Anti-solvent addition THF/Toluene | 4.9% [210] 4.3% toluene in H-NMR | 151.1/185.3*/245.8 | Amorphous [170] Crystal form A[210] |
| Acetic acid Solvate | Crystal form D (08-A17) | Stirring at room temperature $CH_3COOH$ | 16.8% [180] 16.6% acetic acid in H-NMR | 113.1/245.9 | Crystal form A[150] |

Batch prefix: D220 PS -;
[ ]: End-point temperature;
[@]The sample was a mixture of crystal form E + F;
—: crystal form F was unstable at room temperature without further characterization;
*exothermic signal;
[#]Peak temperature;
[&]The data is obtained from the heating experiment of crystal form E (D220-PS-06-A1).

Crystal Form B

Figure 4:
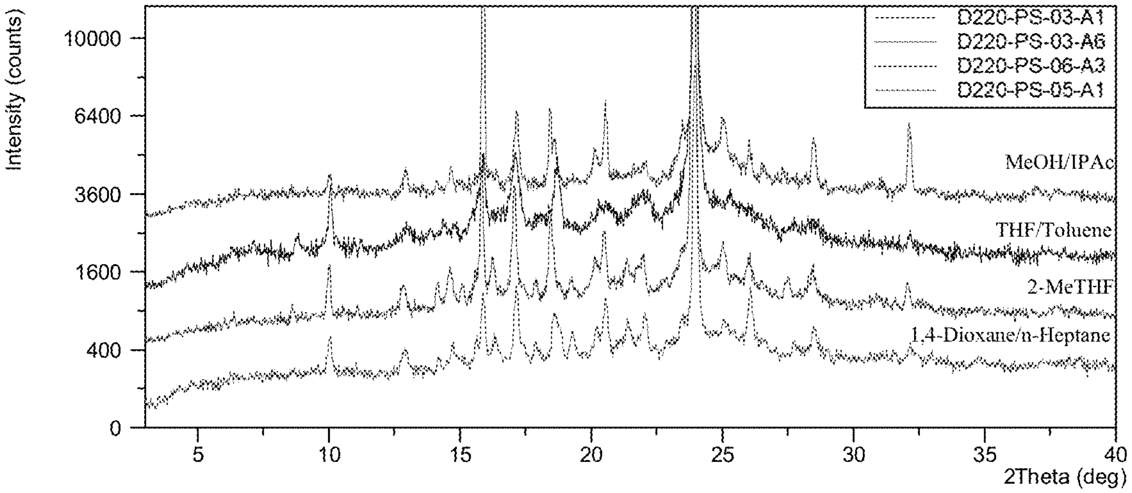
FIG. 4 shows the XRPD pattern of crystal form B.

FIG. 4 shows the XRPD pattern of crystal form B.

Table 1-2 listed summary of XRPD data of crystal form B, with an error range of 2θ values being ±0.2°.

TABLE 1-2

Summary of XRPD data of crystal form B

| 2θ(°) | Intensity |
|---|---|
| 4.645 | 1.60% |
| 8.812 | 2.70% |
| 10.066 | 13.80% |
| 15.861 | 17.70% |
| 17.109 | 16.10% |
| 18.738 | 13.10% |
| 23.947 | 100.00% |
| 32.151 | 4.20% |

Figure 5:
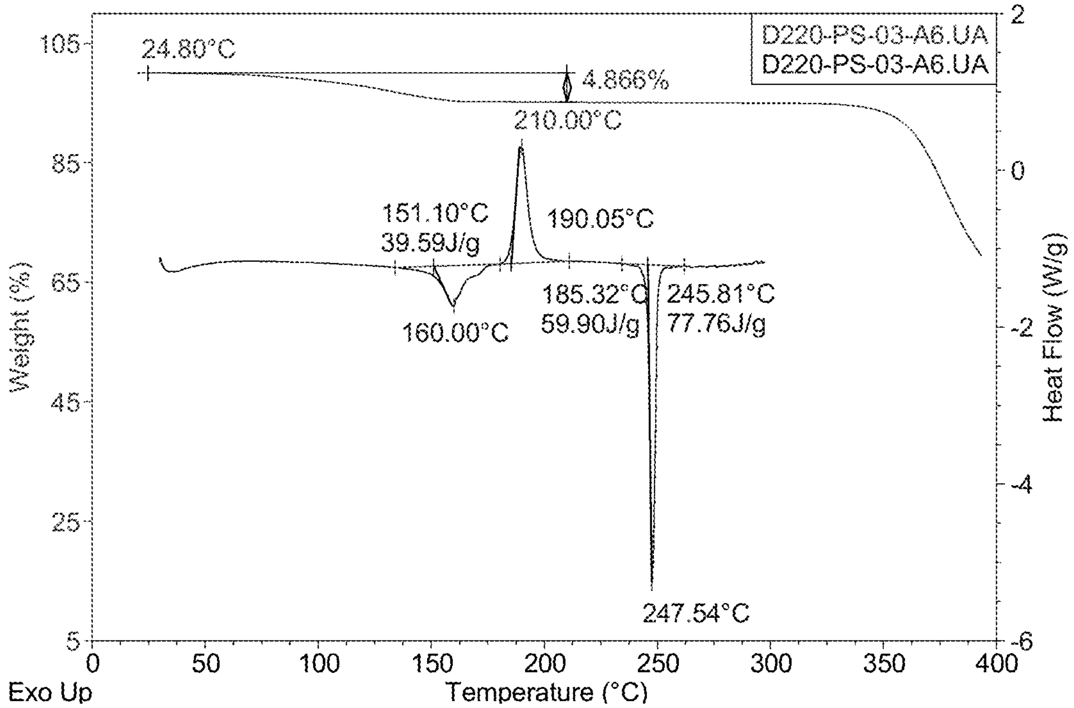
FIG. 5 shows the TGA/DSC pattern of crystal form B (D220-PS-03-A6).

FIG. 5 shows the TGA/DSC pattern of crystal form B (D220-PS-03-A6).

From FIG. 5, it can be seen that the sample has a weight loss of 4.9% before 210° C., with endothermic peaks at 151.1° C. and 245.8° C. (starting point), and an exothermic peak at 185.3° C. (starting point).

Figure 6:
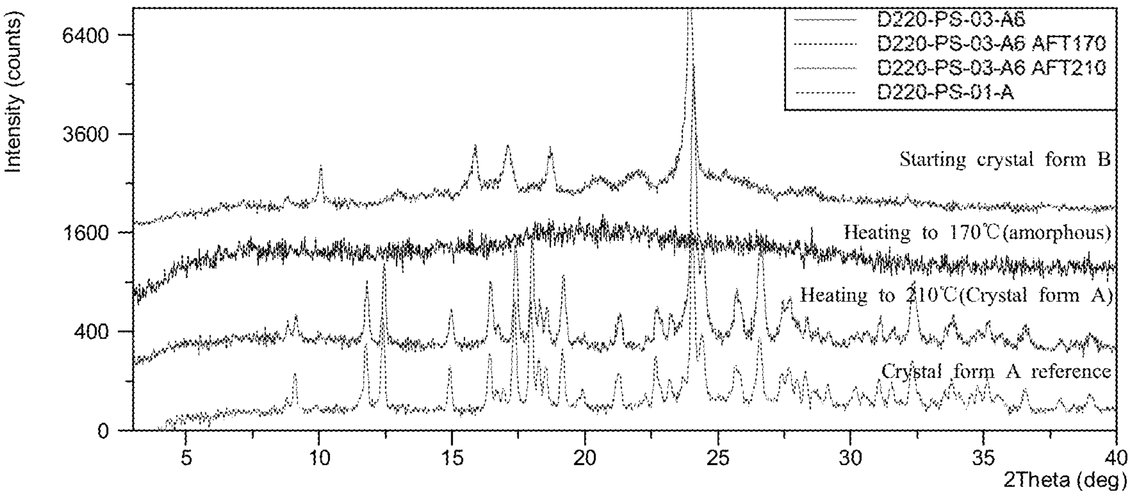
FIG. 6 shows the XRPD comparison pattern of crystal form B (D220-PS-03-A6) before and after heating.

FIG. 6 shows the XRPD comparison pattern of crystal form B (D220-PS-03-A6) before and after heating.

From FIG. 6, it can be seen that crystal form B (D220-PS-03-A6) transformed into amorphous form after heating to 170° C. and then cooling to room temperature under $N_2$ protection; crystal form B transformed into crystal form A after heating to 210° C. and then cooling to room temperature; indicating that the first endothermic peak on DSC was dehydration or desolvation, the exothermic signal was recrystallization of amorphous form, and the second endothermic peak was the melting point of crystal form A.

Figure 7:
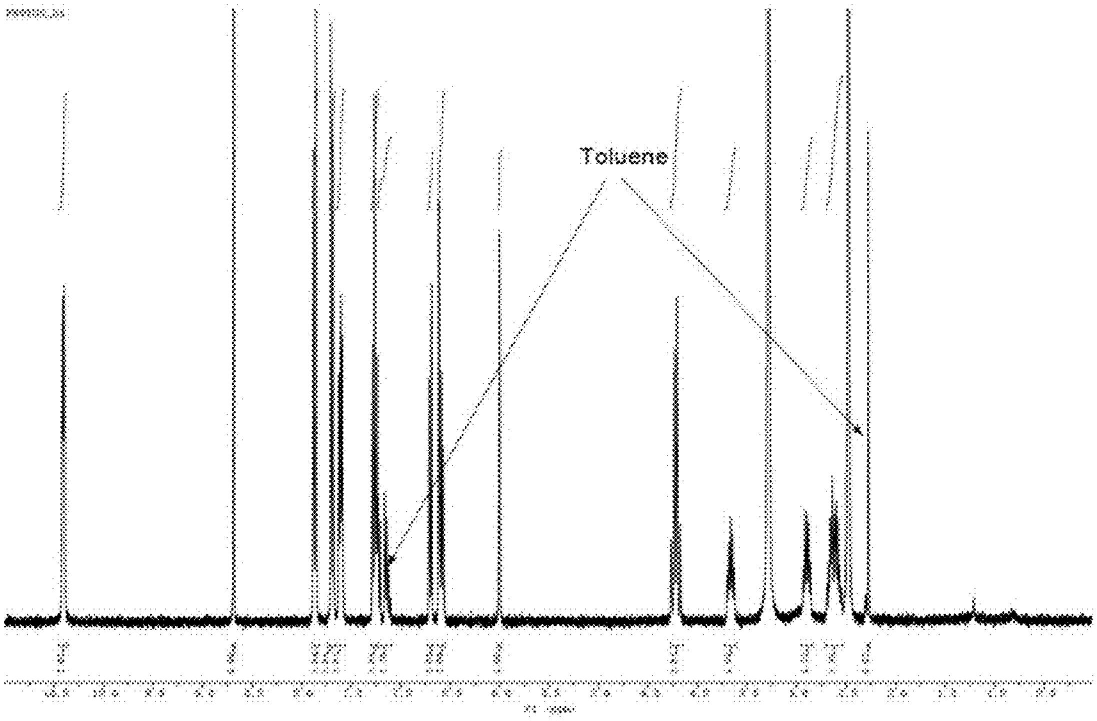
FIG. 7 shows the H-NMR pattern of crystal form B (D220-PS-03-A6).

FIG. 7 shows the H-NMR pattern of crystal form B (D220-PS-03-A6).

From FIG. 7, it can be seen that there is 4.3% of toluene in sample (D220-PS-03-A6), which is close to the weight loss of TGA, indicating that crystal form B was a solvate.

Figure 8:
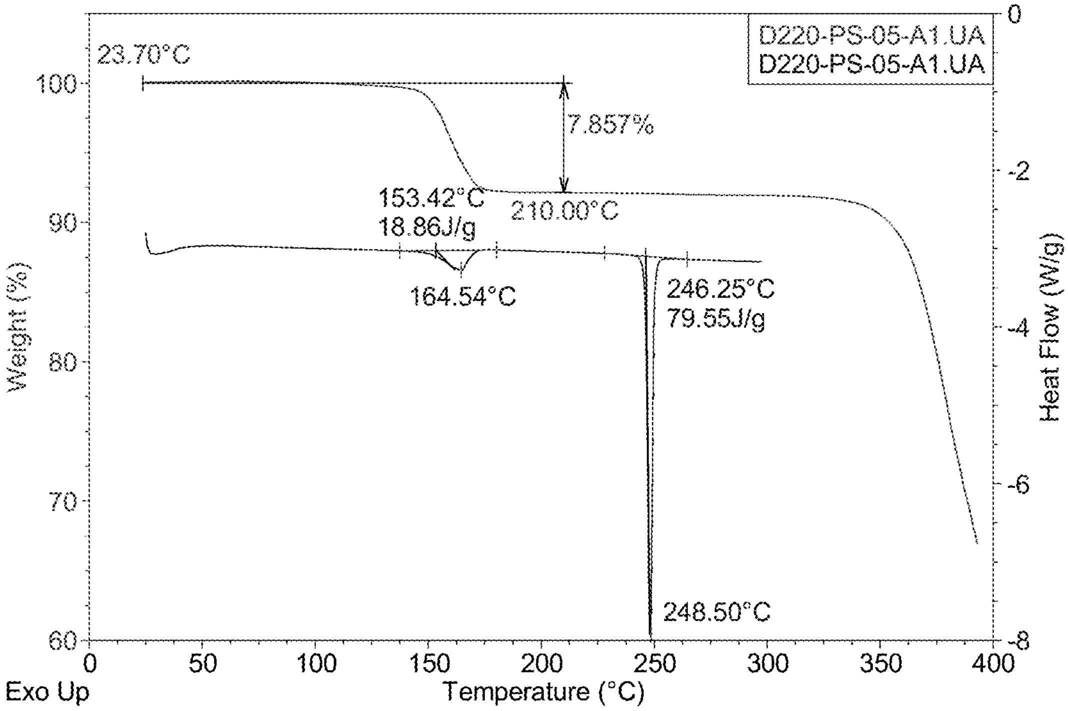
FIG. 8 shows the TGA/DSC pattern of crystal form B (D220-PS-05-A1).

FIG. 8 shows the TGA/DSC pattern of crystal form B (D220-PS-05-A1).

From FIG. 8, it can be seen that the sample has a weight loss of 7.9% before 210° C., and there is an endothermic peak at 153.4° C. (starting point), which is speculated to be dehydration or desolvation taking TGA weight loss into consideration; and a sharp endothermic peak at 246.3° C. (starting point), which is speculated to be melting.

Figure 9:
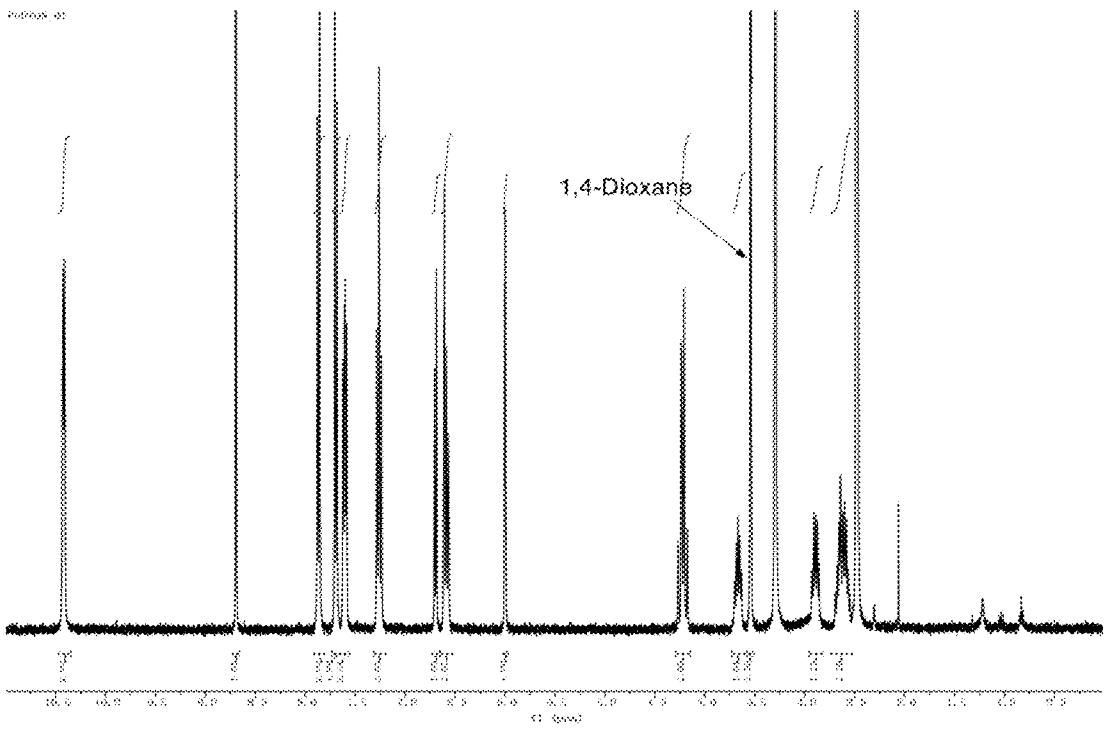
FIG. 9 shows the H-NMR pattern of crystal form B (D220-PS-05-A1).

FIG. 9 shows the H-NMR pattern of crystal form B (D220-PS-05-A1).

From FIG. 9, it can be seen that there is 6.5 wt % of 1,4-Dioxane in sample (D220-PS-05-A1), which is close to the weight loss of TGA, indicating that crystal form B is a solvate.

According to the above data, crystal form B is a solvate and has isomorphism.

Crystal Form D

Figure 10:
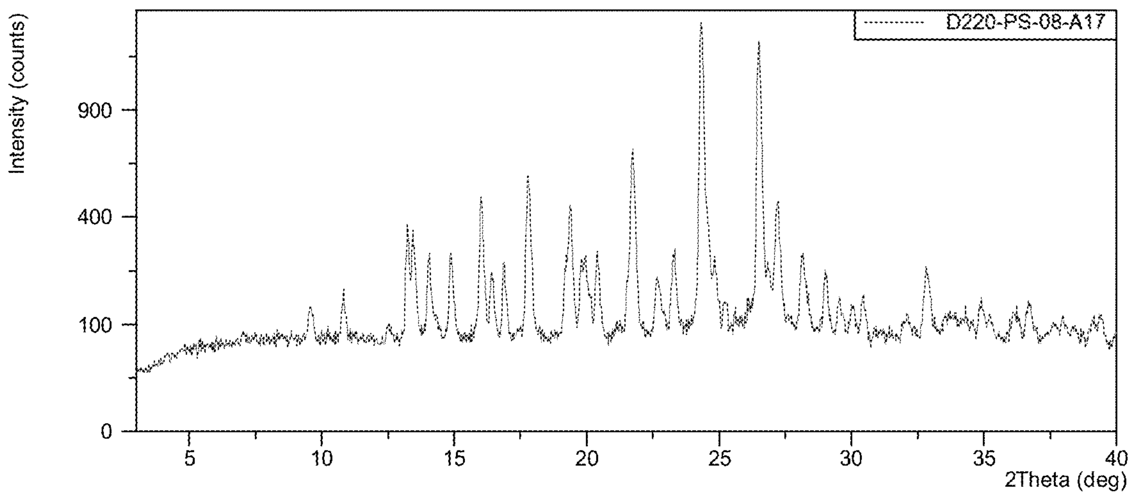
FIG. 10 shows the XRPD pattern of crystal form D.

FIG. 10 shows the XRPD pattern of crystal form D.

Table 1-3 listed summary of XRPD data for crystal form D, with an error range of 2θ values being ±0.2°.

TABLE 1-3

XRPD data for crystal form D

| No. | 2θ(°) | Intensity |
|---|---|---|
| 1 | 9.564 | 4.40% |
| 2 | 10.817 | 7.20% |
| 3 | 12.522 | 2.10% |
| 4 | 13.234 | 21.40% |
| 5 | 13.446 | 20.20% |
| 6 | 14.049 | 14.10% |
| 7 | 14.874 | 14.10% |
| 8 | 16.018 | 29.30% |
| 9 | 16.419 | 10.50% |
| 10 | 16.882 | 12.60% |
| 11 | 17.783 | 36.10% |
| 12 | 19.383 | 27.00% |
| 13 | 19.888 | 11.50% |
| 14 | 20.4 | 15.00% |
| 15 | 21.737 | 44.90% |
| 16 | 22.664 | 8.60% |
| 17 | 23.296 | 12.40% |
| 18 | 24.324 | 100.00% |
| 19 | 24.833 | 12.70% |
| 20 | 25.225 | 3.50% |
| 21 | 26.505 | 91.10% |
| 22 | 27.214 | 25.90% |
| 23 | 28.146 | 12.20% |
| 24 | 29.031 | 9.70% |
| 25 | 29.52 | 4.50% |
| 26 | 30.041 | 3.50% |
| 27 | 30.426 | 6.20% |
| 28 | 32.097 | 3.40% |
| 29 | 32.839 | 10.30% |
| 30 | 33.768 | 2.20% |
| 31 | 34.905 | 5.50% |
| 32 | 35.215 | 3.40% |
| 33 | 36.192 | 2.70% |
| 34 | 36.698 | 4.70% |
| 35 | 37.977 | 3.10% |
| 36 | 39.129 | 2.20% |
| 37 | 39.383 | 2.80% |

Figure 11:
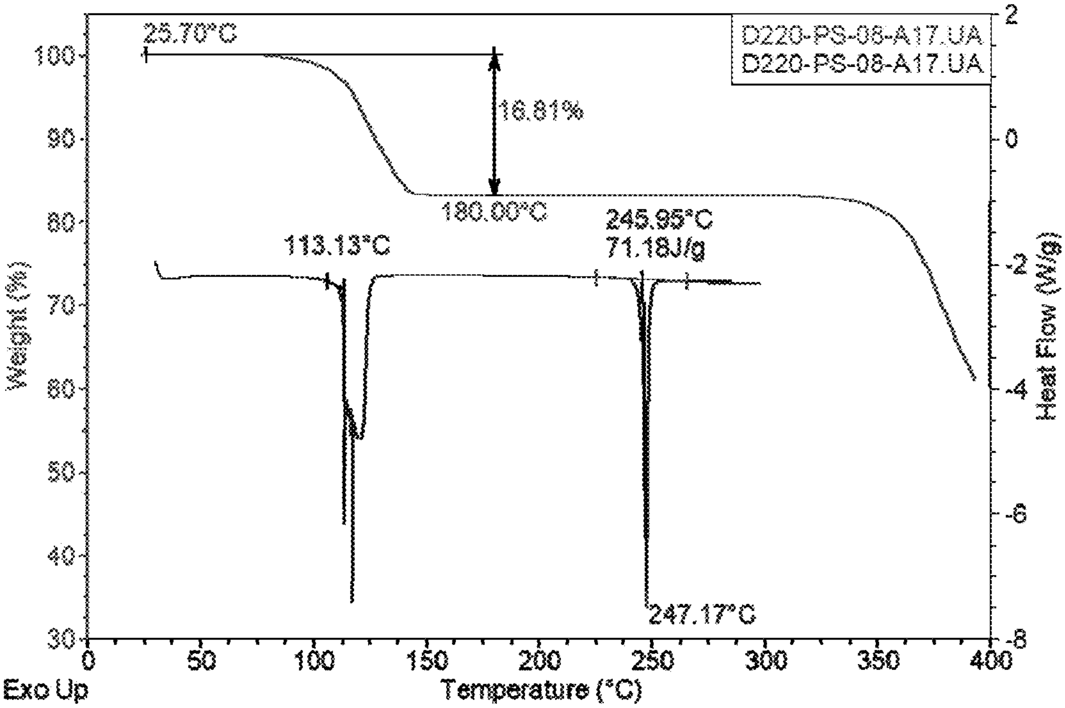
FIG. 11 shows the TGA/DSC pattern of crystal form D(D220-PS-08-A17).

FIG. 11 shows the TGA/DSC pattern of crystal form D(D220-PS-08-A17).

From FIG. 11, it can be seen that the sample has a weight loss of 16.8% before 180° C., and there is an endothermic peak at 113.1° C. (starting point), which is speculated to be dehydration or desolvation taking TGA weight loss into consideration; and a sharp endothermic peak at 245.9° C. (starting point), which is speculated to be melting.

Figure 12:
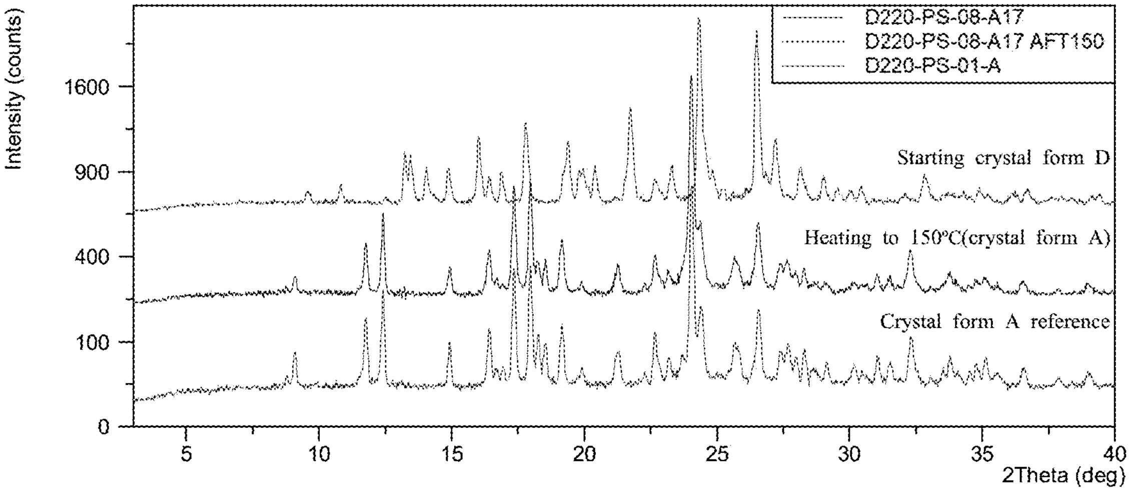
FIG. 12 shows the XRPD comparison pattern of crystal form D (D220-PS-08-A17) before and after heating.

FIG. 12 shows the XRPD comparison pattern of crystal form D (D220-PS-08-A17) before and after heating.

From FIG. 12, it can be seen that crystal form D(D220-PS-08-17) transformed into crystal form A after heating to 150° C. and then cooling to room temperature under $N_2$ protection, indicating that crystal form D was a hydrate or solvate.

Figure 13:
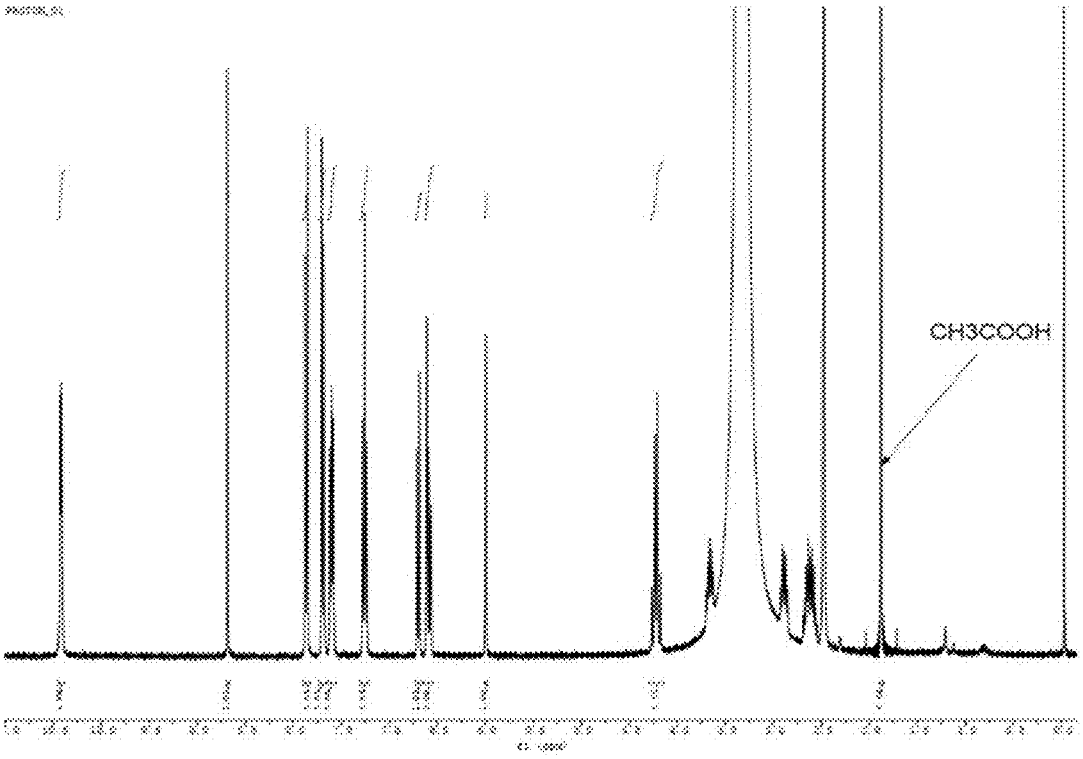
FIG. 13 shows the H-NMR pattern of crystal form D(D220-PS-08-A17).

FIG. 13 shows the H-NMR pattern of crystal form D(D220-PS-08-A17).

From FIG. 13, it can be seen that there is 16.6 wt % $CH_3COOH$ in the sample, which is close to the TGA results, indicating that crystal form D is an acetic acid solvate.

Crystal Form E

Figure 14:
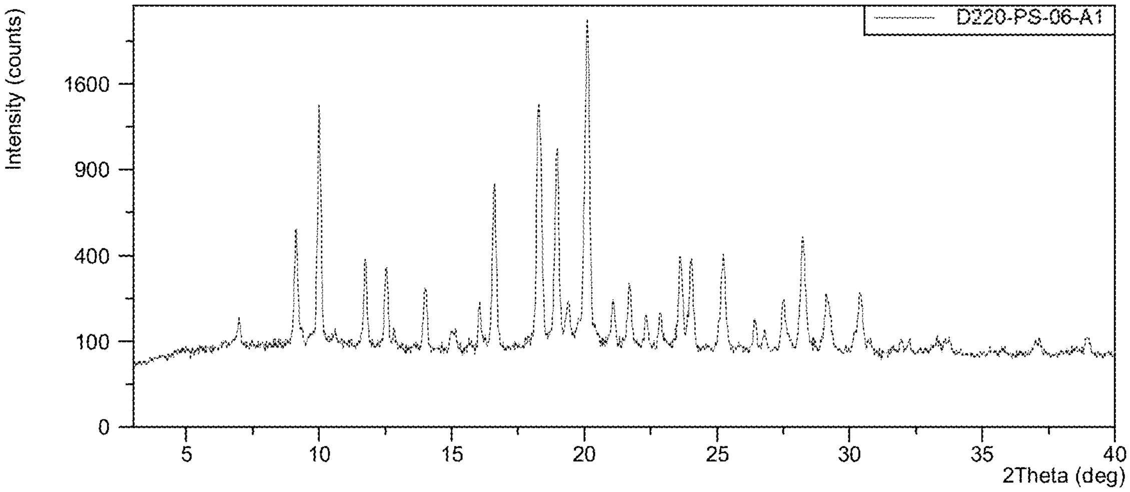
FIG. 14 shows the XRPD pattern of crystal form E(D220-PS-06-A1).

FIG. 14 shows the XRPD pattern of crystal form E(D220-PS-06-A1).

Table 1-4 listed summary of XRPD data for crystal form E, with an error range of 2θ values being ±0.2°.

TABLE 1-4

XRPD data for crystal form E

| No. | 2θ(°) | Intensity |
|---|---|---|
| 1 | 6.984 | 3.20% |
| 2 | 9.132 | 20.40% |
| 3 | 10.002 | 59.70% |
| 4 | 10.597 | 1.50% |
| 5 | 11.745 | 13.70% |
| 6 | 12.538 | 11.70% |
| 7 | 12.824 | 2.20% |
| 8 | 14.006 | 8.00% |
| 9 | 15.066 | 1.80% |
| 10 | 15.721 | 0.90% |
| 11 | 16.057 | 5.70% |
| 12 | 16.607 | 33.40% |
| 13 | 18.287 | 59.90% |
| 14 | 18.969 | 41.90% |
| 15 | 19.39 | 5.10% |
| 16 | 20.115 | 100.00% |
| 17 | 21.085 | 5.70% |
| 18 | 21.701 | 8.70% |
| 19 | 22.327 | 3.80% |
| 20 | 22.872 | 4.30% |
| 21 | 23.626 | 13.80% |
| 22 | 24.022 | 12.50% |
| 23 | 25.243 | 14.40% |
| 24 | 25.834 | 0.70% |
| 25 | 26.431 | 3.20% |
| 26 | 26.802 | 2.10% |
| 27 | 27.509 | 6.40% |
| 28 | 28.238 | 18.80% |
| 29 | 29.151 | 7.10% |
| 30 | 30.392 | 7.80% |
| 31 | 30.738 | 1.20% |
| 32 | 31.95 | 1.30% |
| 33 | 32.261 | 1.30% |
| 34 | 33.301 | 1.80% |
| 35 | 33.682 | 1.00% |
| 36 | 37.098 | 0.80% |
| 37 | 38.968 | 1.60% |

Figure 15:
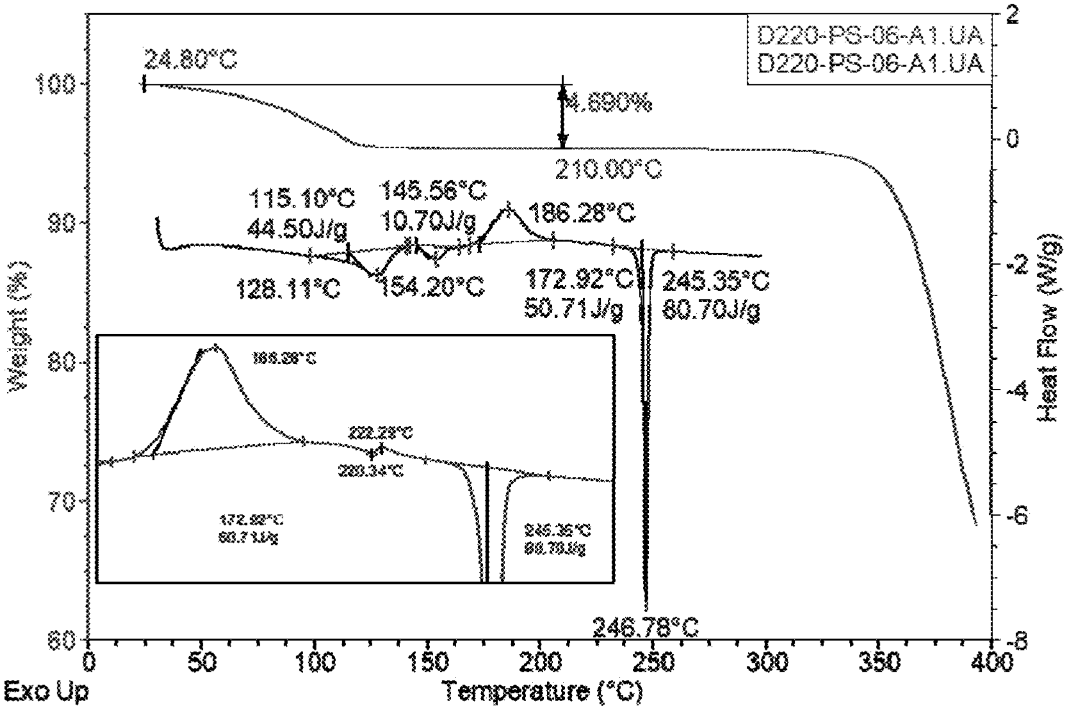
FIG. 15 shows the TGA/DSC pattern of crystal form E(D220-PS-06-A1).

FIG. 15 shows the TGA/DSC pattern of crystal form E(D220-PS-06-A1).

From FIG. 15, it can be seen that the sample has a weight loss of 4.7% before 210° C., and there are endothermic peaks at 115.1° C. and 145.6° C. (starting point), which is speculated to be stepwise dehydration or desolvation taking TGA weight loss into consideration. There is an exothermic peak at 172.9° C. (starting point), which is speculated to be recrystallization of amorphous form. There are endothermic/exothermic peaks respectively at 220.3° C./222.3° C. (peak values), which is speculated to be solid phase transition. There is a sharp endothermic peak at 245.4° C. (starting point), which is speculated to be a melting point.

Figure 16:
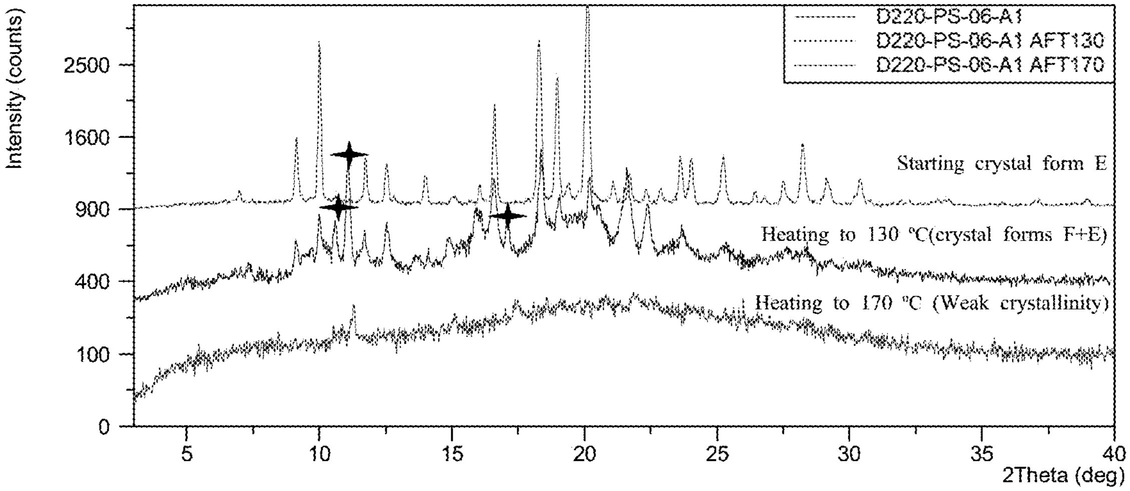
FIGS. 16 and 17 show the XRPD comparison pattern of crystal form E (D220-PS-06-A1) before and after heating (I/II).
Figure 17:
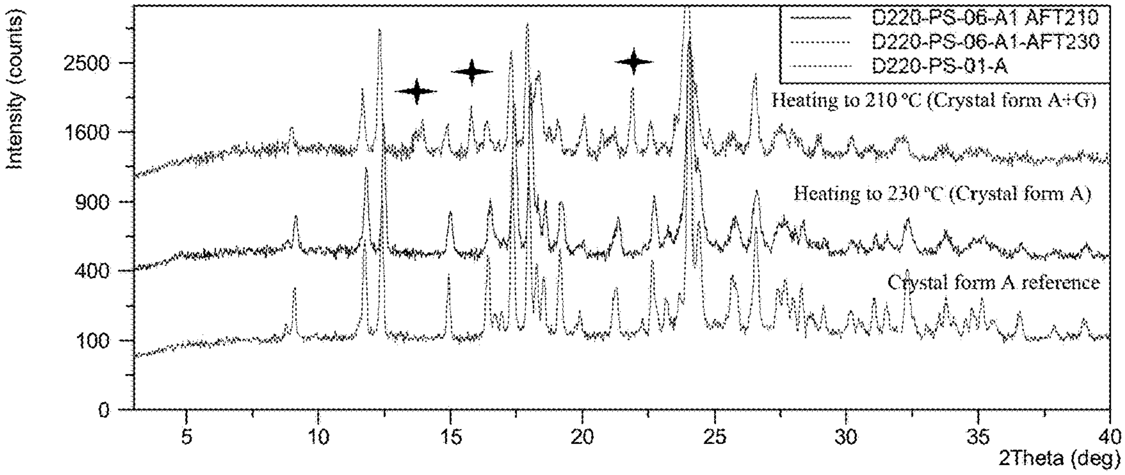

FIGS. 16 and 17 show the XRPD comparison patterns of crystal form E (D220-PS-06-A1) before and after heating (I/II).

From FIGS. 16 and 17, it can be seen that crystal form E transformed partially into new crystal form F after heating to 130° C. under $N_2$ protection, indicating that crystal form E is a hydrate or solvate. When heating to 170° C., the sample has weak crystallinity. When heating to 210° C., most of the sample transformed into crystal form A, and a new diffraction peak named crystal form G was observed. When heating to 230° C., the sample transformed into crystal form A.

Crystal form F

Crystal form F can be obtained by dehydration of hydrate crystal form E, but can not be obtained from solution method. New diffraction peaks were observed when crystal form E (D220-PS-06-A1) was heated to 130° C. and then cooling to room temperature under $N_2$ protection, and named crystal form F, which is speculated to be an amorphous form.

Figure 18:
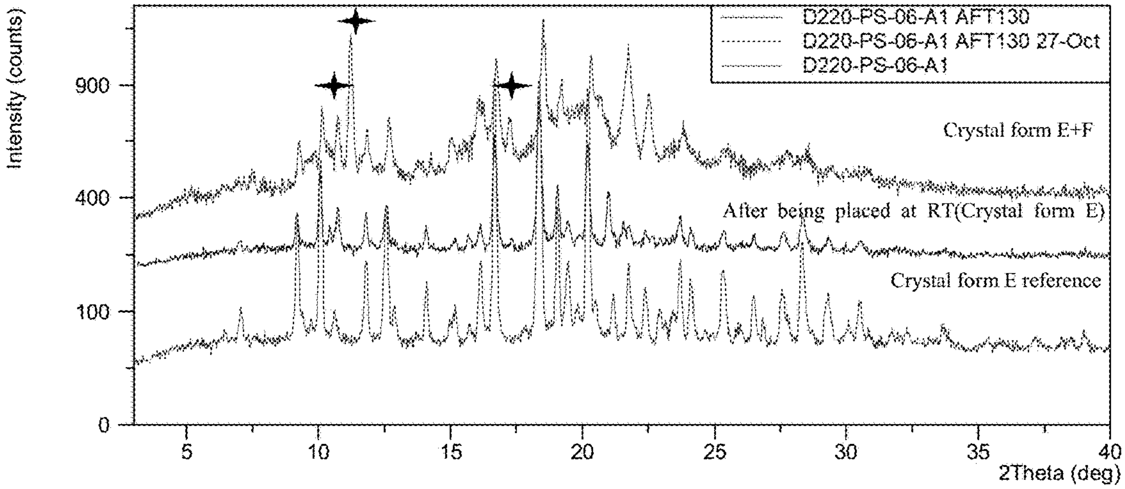
FIG. 18 shows the XRPD comparison pattern of crystal form F (D220-PS-06-A1 AFT130) before and after room temperature storage.

Crystal form F (D220-PS-06-A1 AFT130) transformed into crystal form E (FIG. 18) after being placed at room temperature (18-20° C./45~75% RH) for about 3 days (FIG. 18), indicating that crystal form F was unstable under room temperature conditions.

Figure 21:
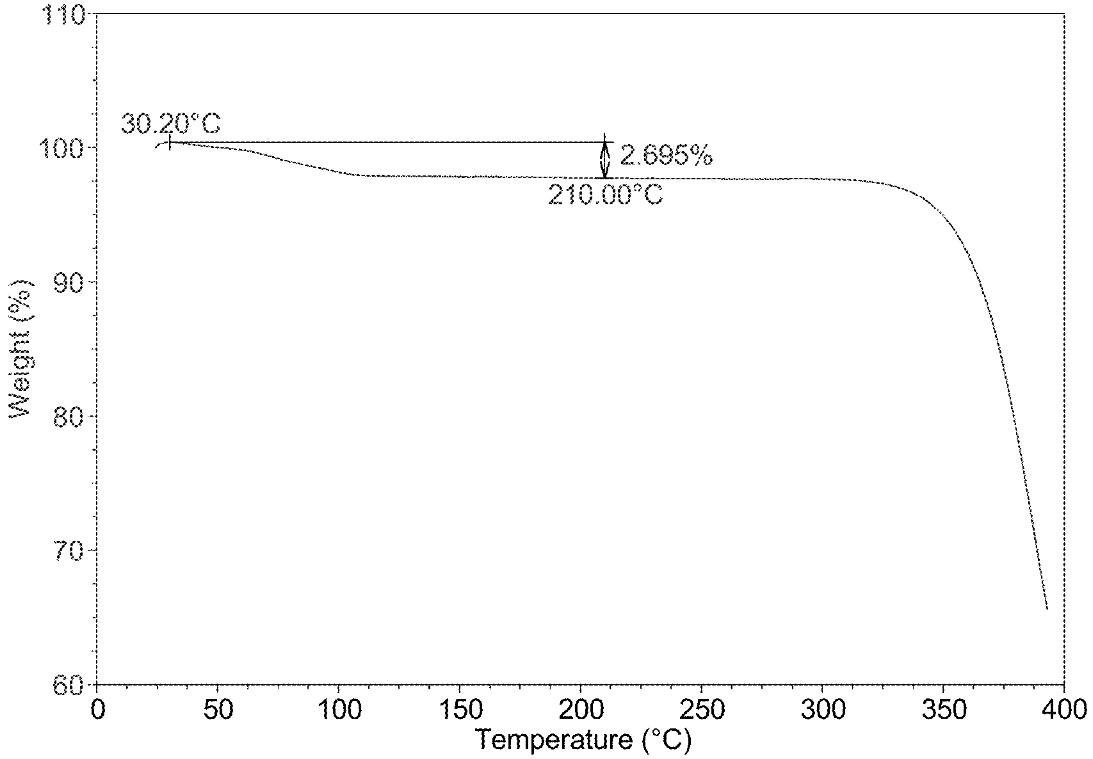
FIG. 21 shows the TGA pattern of crystal form F(D220-PS-06-A1 AFT130) transformed into crystal form E after room temperature storage.

FIG. 21 shows the TGA pattern of crystal form F(D220-PS-06-A1 AFT130) transforming into crystal form E after room temperature storage.

From FIG. 21, it can be seen that there is a 2.7% weight loss before 210° C., indicating that crystal form E is a hydrate.

Table 1-5 listed summary of XRPD data of crystal form F, with an error range of 2θ values being ±0.2°.

TABLE 1-5

| XRPD data for crystal form F | | |
|---|---|---|
| No. | 2θ(°) | Intensity |
| 1 | 5.193 | 9.10% |
| 2 | 7.498 | 10.00% |
| 3 | 9.246 | 26.20% |
| 4 | 10.153 | 41.10% |
| 5 | 10.749 | 36.40% |
| 6 | 11.228 | 100.00% |
| 7 | 11.851 | 31.70% |
| 8 | 12.692 | 30.10% |
| 9 | 13.804 | 8.60% |
| 10 | 14.252 | 13.00% |
| 11 | 15.057 | 18.30% |
| 12 | 16.05 | 40.40% |
| 13 | 16.737 | 69.00% |
| 14 | 17.255 | 22.20% |
| 15 | 18.503 | 96.80% |
| 16 | 19.21 | 41.70% |
| 17 | 20.331 | 63.60% |
| 18 | 20.687 | 35.00% |
| 19 | 21.753 | 76.70% |
| 20 | 22.536 | 41.00% |
| 21 | 23.846 | 14.00% |
| 22 | 25.474 | 7.50% |

Crystal Form G

Figure 19:
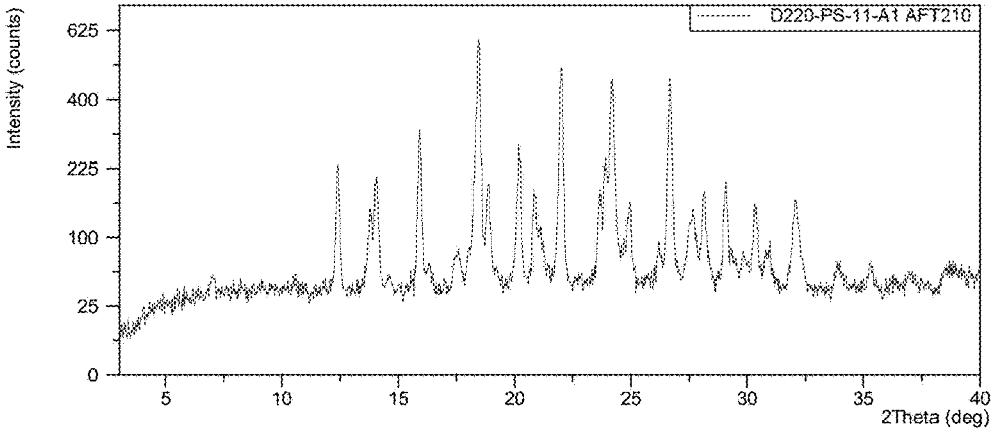
FIG. 19 shows the XRPD pattern of crystal form G.

Crystal form G can be obtained by solid-phase transformation after dehydration of hydrate crystal form E, but cannot be obtained from solution method. New crystal form G was obtained by heating hydrate crystal form E to 210° C. and then cooling to room temperature under $N_2$ protection. The XRPD results are shown in FIG. 19.

Table 1-6 listed summary of XRPD data for the crystal form G, with an error range of 2θ values being ±0.2°.

TABLE 1-6

| XRPD data for crystal form G | | |
|---|---|---|
| No. | 2θ(°) | Intensity |
| 1 | 5.489 | 1.80% |
| 2 | 7.041 | 3.40% |
| 3 | 10.559 | 3.40% |
| 4 | 12.411 | 36.80% |
| 5 | 13.815 | 19.80% |
| 6 | 14.045 | 31.10% |
| 7 | 14.587 | 3.60% |
| 8 | 15.905 | 47.90% |
| 9 | 16.334 | 5.00% |
| 10 | 17.534 | 6.70% |
| 11 | 18.452 | 100.00% |
| 12 | 18.872 | 27.00% |
| 13 | 20.186 | 41.80% |
| 14 | 20.847 | 23.70% |
| 15 | 21.088 | 12.10% |
| 16 | 22.004 | 82.00% |

TABLE 1-6-continued

| XRPD data for crystal form G | | |
|---|---|---|
| No. | 2θ(°) | Intensity |
| 17 | 23.682 | 22.90% |
| 18 | 23.922 | 37.50% |
| 19 | 24.202 | 75.90% |
| 20 | 24.935 | 18.90% |
| 21 | 26.177 | 8.00% |
| 22 | 26.664 | 75.90% |
| 23 | 27.652 | 18.40% |
| 24 | 28.137 | 23.70% |
| 25 | 29.075 | 26.20% |
| 26 | 29.875 | 5.10% |
| 27 | 30.333 | 20.10% |
| 28 | 30.889 | 6.10% |
| 29 | 32.077 | 21.10% |
| 30 | 33.922 | 5.40% |
| 31 | 35.293 | 5.90% |
| 32 | 38.538 | 4.50% |
| 33 | 38.674 | 5.00% |

Figure 20:
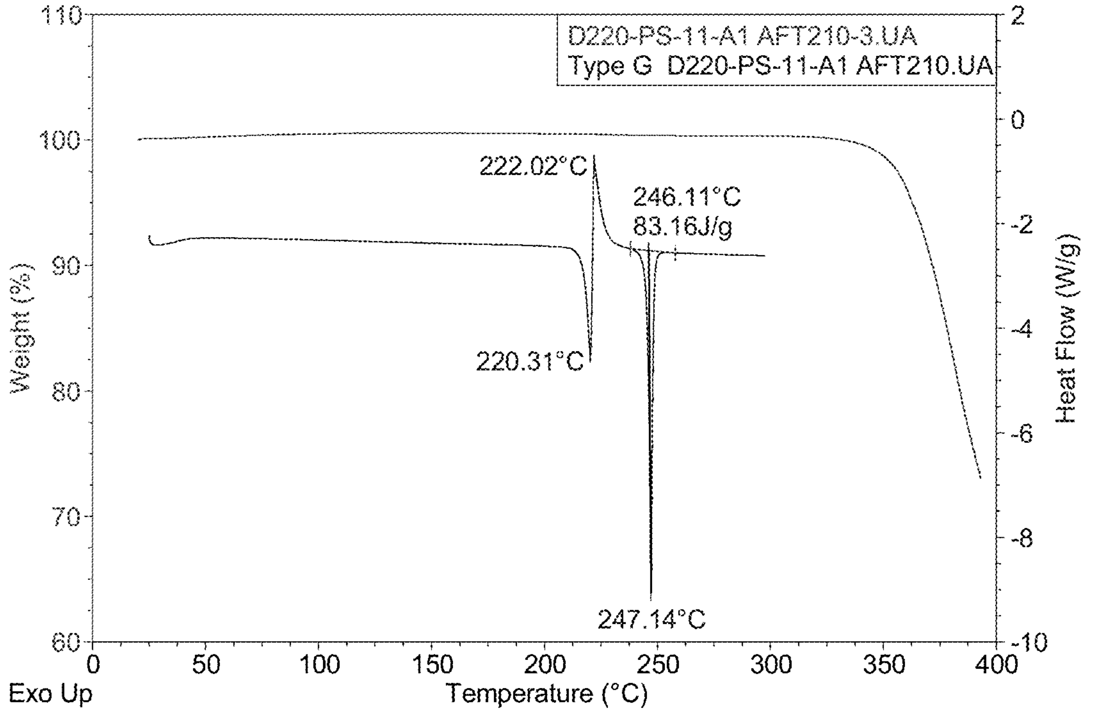
FIG. 20 shows the TGA/DSC pattern of crystal form G.

FIG. 20 shows the TGA/DSC pattern of crystal form G.

From FIG. 20, it can be seen that the sample almost has no weight loss before decomposition, with endothermic/exothermic peaks at 220.3° C. and 222.0° C. (peak value), respectively, and a sharp endothermic peak at 246.1° C. (starting point).

Taking FIG. 17 into consideration, it is indicated that crystal form G is an anhydrous crystal form.

Figure 22:
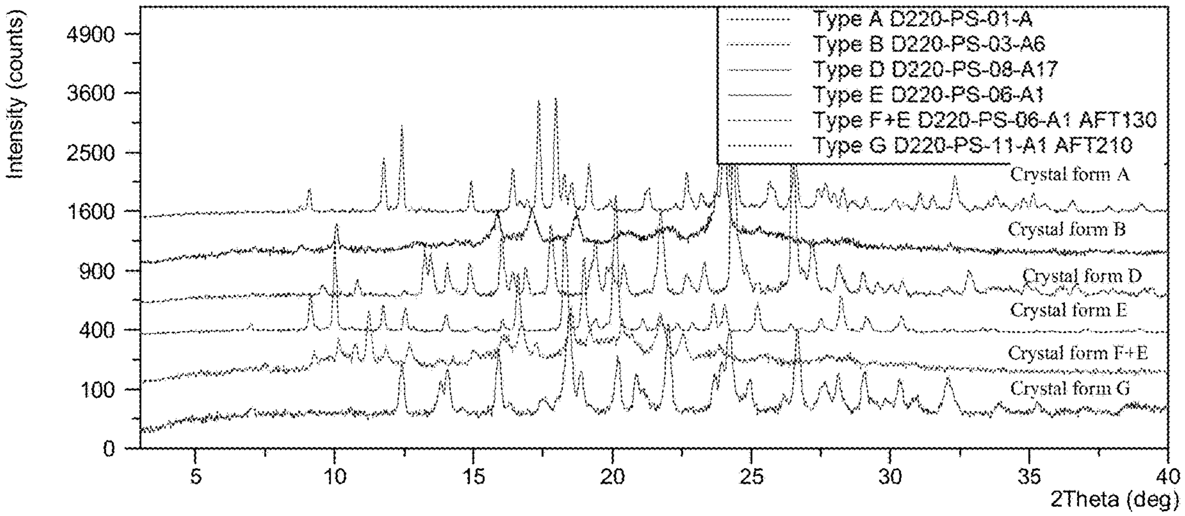
FIG. 22 shows the XRPD comparison pattern of crystal forms A/B/D/E/F/G.

FIG. 22 shows the XRPD comparison pattern of crystal forms A/B/D/E/F/G.

From FIG. 22, it can be seen that compound I has six crystal forms, including four found in crystal form screening experiments (named crystal form A/B/D/E) and two found in subsequent crystal form identification (named crystal form F/G). Among them, three are anhydrous crystal forms (crystal form A/F/G), one is hydrate (crystal form E), and two are solvate (crystal form B/D).

Example 3: Studies on Relationship Between Crystal Forms

Studies on Relationship between Anhydrous Crystal Forms

A total of three anhydrous crystal forms were discovered in crystal form research, among which crystal form F was unstable at room temperature and transformed into hydrate crystal form E after placement. In order to study the stability relationship between other anhydrous crystal forms (crystal forms A/G), suspension competition experiments were conducted at room temperature and 60° C. using ACN and EtOAc as solvents. The specific operations were as follows: 4 portions of excess crystal form A was weighed into 4 HPLC vials, 0.5 mL ACN was added to 2 portions, and 0.5 mL EtOAc was added to the other 2 portions, then placed them at room temperature and 60° C. with magnetic stirring for ~2 h, respectively, and then go through preheated nylon membranes (with a pore size of 0.22 μm) to get saturated solution; ~4 mg anhydrous crystal form A/G of Compound I was added to the saturated filtrate, respectively, and then magnetically stirred for ~2 h at room temperature or 60° C.; centrifuged to separate the solid for XRPD testing.

Figure 23:
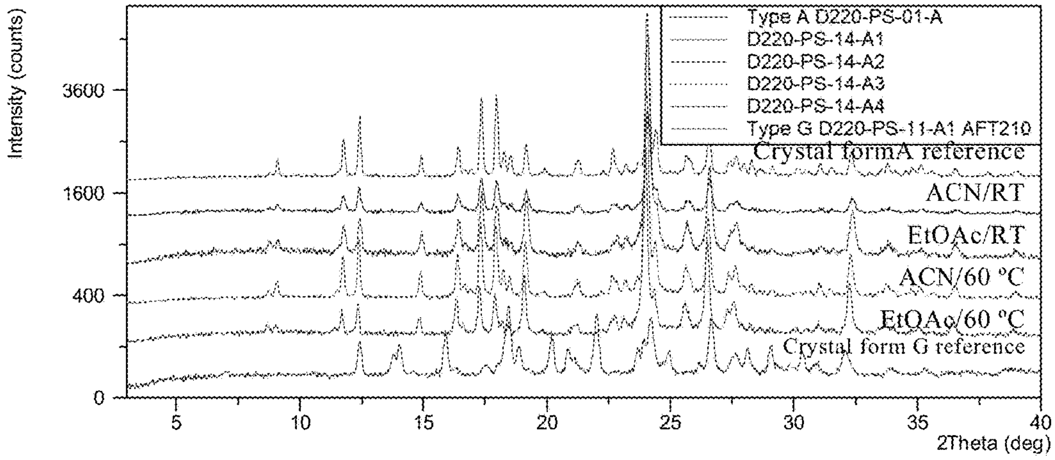
FIG. 23 shows the XRPD comparison pattern of crystal form A/G in suspension competition experiment.

Results (table 1-7) indicated that the solid obtained in both solvents at room temperature and 60° C. were crystal form A. Taking the fact that crystal form G transformed into crystal form A after post-melting recrystallization into consideration, it indicates that crystal form A is thermodynamically more stable than crystal form G. The XRPD results are shown in FIG. 23.

TABLE 1-7

| Suspensioncompetition results of anhydrous crystal form A/G of compound I at room temperature and 60° C. | | | | |
|---|---|---|---|---|
| Test number | Starting crystal form | Solvent | Temperature(° C.) | The crystal form obtained |
| D220-PS-14-A1 | Crystal form A/G | ACN | Room temperature(~18) | Crystal form A |
| D220-PS-14-A2 | | EtOAc | | Crystal form A |
| D220-PS-14-A3 | | ACN | 60 | Crystal form A |
| D220-PS-14-A4 | | EtOAc | | Crystal form A |

Key Water Activity Research

The study on the relationship between anhydrous crystal forms of compound I shows that the anhydrous crystal form A is the most stable one at room temperature. Therefore, crystal form A and hydrate crystal form E were selected for key water activity studies. Specifically, Mixed solvents of Acetone/$H_2O$ with a target water activity ($a_w$ of 0/0.2/0.4/0.6/0.8/1.0) were prepared at room temperature for use; water activity of Acetone/$H_2O$ system with corresponding volume ratio see table 1-8. ~20 mg of crystal form A samples were weighed separately into the corresponding solvent, stirred at room temperature for 2 ~hours to obtain a suspension, and the suspension was filtered with a nylon membrane (pore size: 0.22 μm) to get filtrate. ~4 mg of hydrate crystal form E and crystal form A of compound I were weighted into HPLC vials, the aforementioned filtrate was added, and stirred at room temperature for 3-13 days to collect XRPD data.

Figure 24:
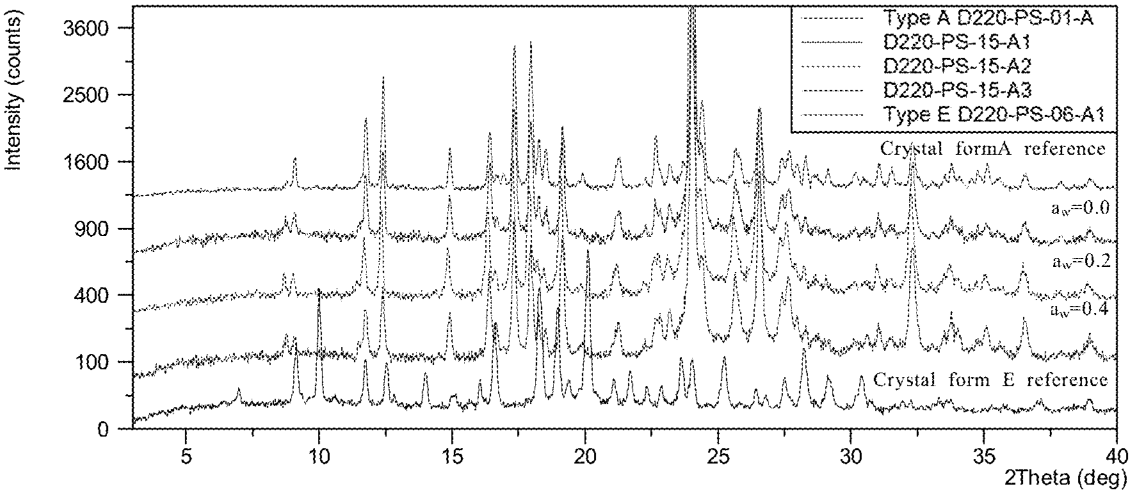
FIG. 24 and FIG. 25 are the XRPD patterns of the solid obtained from the key water activity experiment at room temperature.
Figure 25:
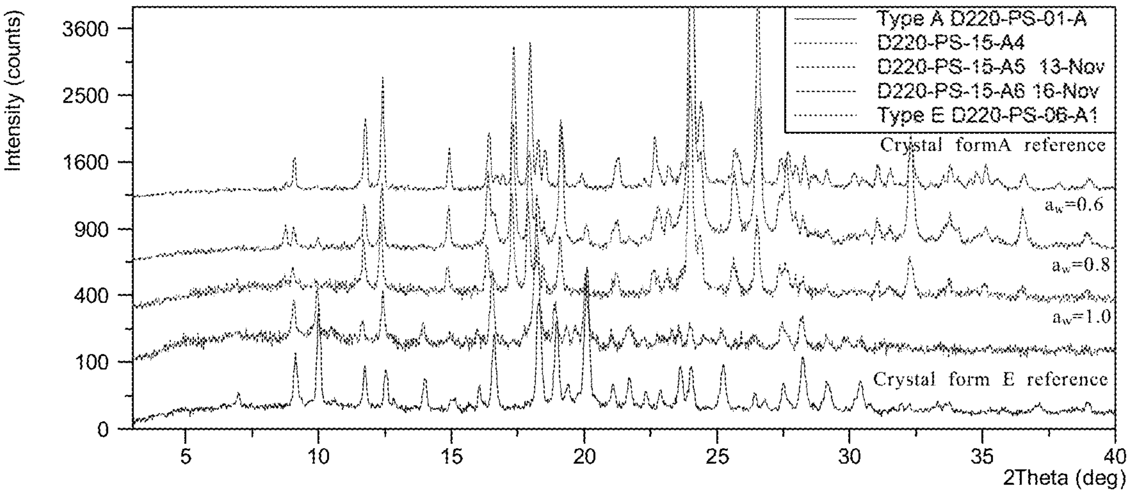

The experimental results (table 1-8 and FIG. 24/25) show that when the water activity ($a_w$) is between 0 and 0.8, the solid obtained is anhydrous crystal form A of compound I; when the water activity is 1.0, the solid obtained is hydrate crystal form E. This indicates that when the water activity is between 0 and 0.8 at room temperature, anhydrous crystal form A of compound I is more stable, and when the water activity is 1.0, the hydrate crystal form E is more stable. The key water activity for hydrate crystal form E and anhydrous crystal form A of compound I is between 0.8 and 1.0.

TABLE 1-8

| Results of key water activity of anhydrous crystal form A, and hydrate crystal form E of compound I at room temperature | | | |
|---|---|---|---|
| Test number | Water activity($A_w$) | Acetone/$H_2O$, v/v | The crystal form obtained |
| D220-PS-15-A1 | 0 | 1000:0 | Crystal form A |
| D220-PS-15-A2 | 0.2 | 984:16 | Crystal form A |

TABLE 1-8-continued

| Results of key water activity of anhydrous crystal form A, and hydrate crystal form E of compound I at room temperature | | | |
|---|---|---|---|
| Test number | Water activity($A_w$) | Acetone/$H_2O$, v/v | The crystal form obtained |
| D220-PS-15-A3 | 0.4 | 948:52 | Crystal form A |
| D220-PS-15-A4 | 0.6 | 857:143 | Crystal form A |
| D220-PS-15-A5 | 0.8 | 604:396 | Crystal form A |
| D220-PS-15-A6 | 1.0 | 0:1000 | Crystal form E |

Example 4 Research on the Performance of Druggability

Hygroscopicity

Hygroscopicity of anhydrous crystal form A of compound I was evaluated using DVS at 25° C. Before evaluation, anhydrous crystal form A of compound I was equilibrated under 0% RH conditions to remove water or solvent adsorbed on the surface.

Figure 26:
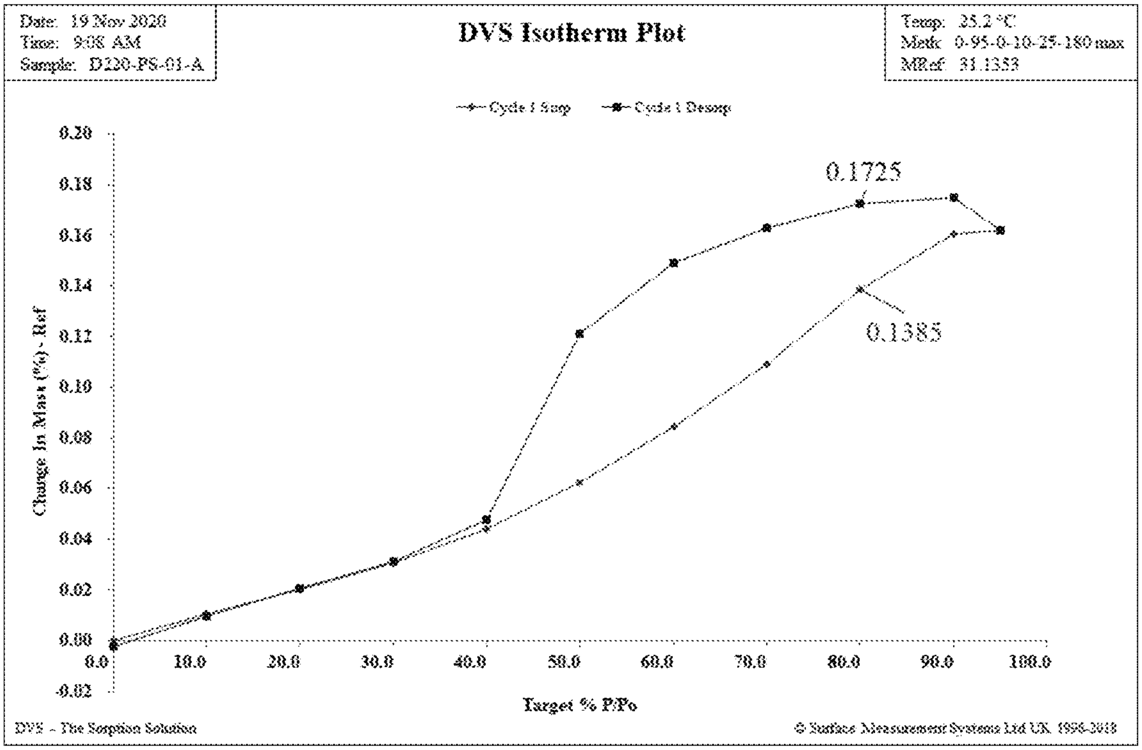
FIG. 26 shows the DVS pattern of crystal form A.
Figure 27:
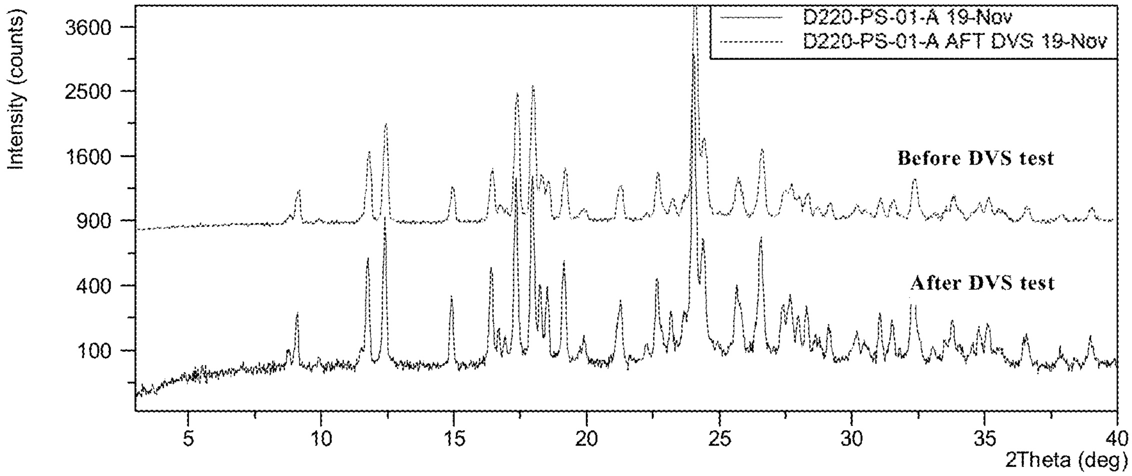
FIG. 27 shows the XRPD comparison pattern of crystal form A before and after DVS test.

From FIG. 26, it can be seen that anhydrous crystal form A of compound I has a weight gain of 0.14% at 80% RH, indicating that the sample is hardly hygroscopic. The sample remains unchanged (FIG. 27) after testing, indicating good crystal form stability.

Solid-State Stability

To evaluate the solid-state stability of the preferred crystal form (anhydrous crystal form A of compound I), ~20 mg sample was weighed in an HPLC vial and then placed open under the following three conditions: 1) 25° C./60% RH, 2) 40° C./75% RH, and 3) 60° C. Purity tests (HPLC) and crystal form detection (XRPD) were performed on starting samples, samples stored for one week and two weeks.

Figure 28:
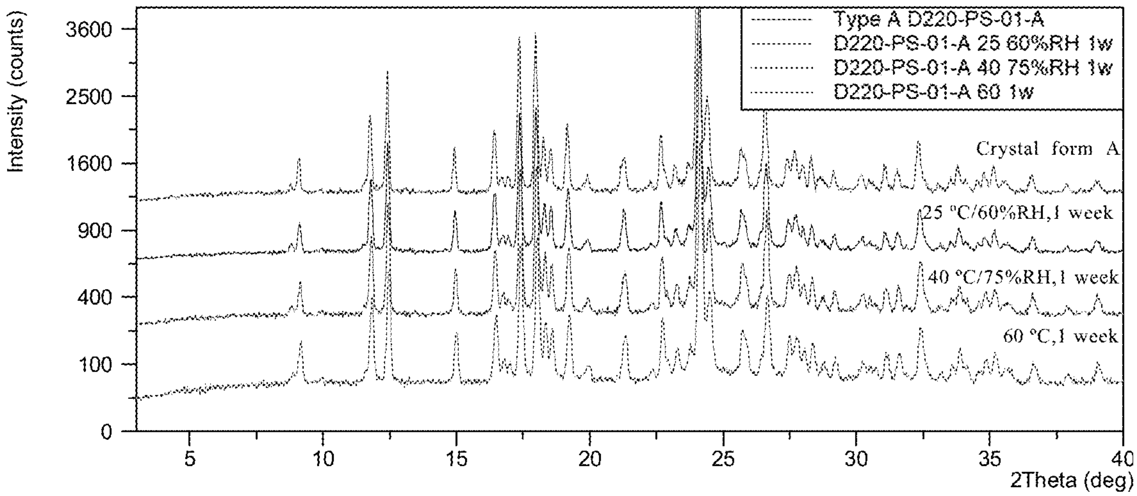
FIG. 28 shows the XRPD comparison pattern of crystal form A in one week stability test.
Figure 29:
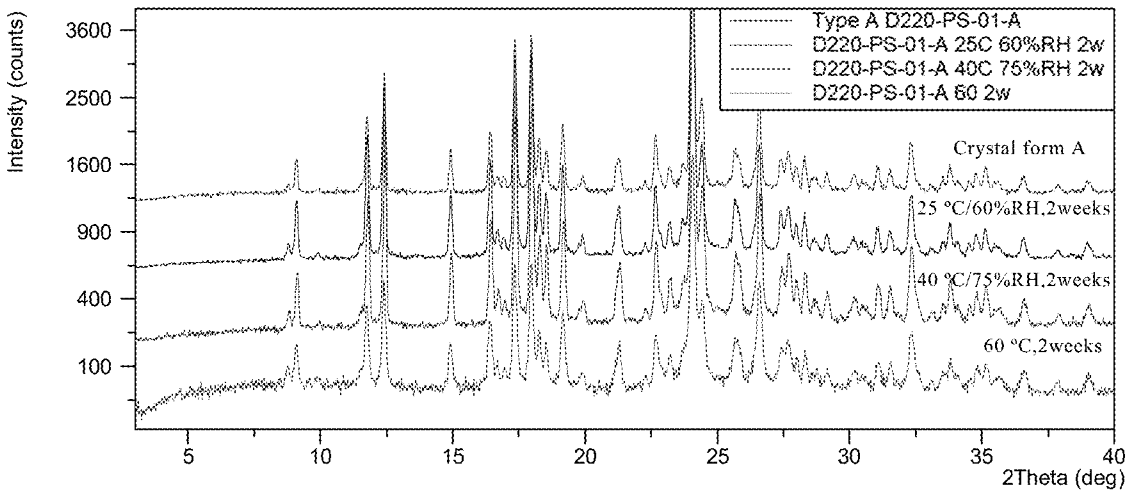
FIG. 29 shows the XRPD comparison pattern of crystal form A in two week stability test.

The results showed that crystal form A remained unchanged after being placed under selected conditions for one and two weeks (FIG. 28 and FIG. 29), and there was no significant change in purity (table 1-9), indicating that crystal form A has good solid-state stability.

TABLE 1-9

| Summary of two week stability of crystal form A | | | | | | |
|---|---|---|---|---|---|---|
| | | | 1 week | | 2 week | |
| Starting sample | | | | Change in | | change in |
| Crystal form | Purity(Area %) | Condition | Purity(Area %) | Crystal form | Purity(Area %) | Crystal form |
| Crystal form A | 99.12 | 25° C./ 60% RH | 99.08 | Unchanged | 99.12 | Unchanged |
| | | 40° C./ | 99.07 | | 99.14 | |
| | | 75% RH | 99.09 | | 99.13 | |
| | | 60° C. | | | | |

Results

1) Anhydrous crystal form A of compound I is hardly hygroscopic and the crystal form is unchanged before and after DVS test, demonstrating good crystal form stability;
2) Crystal form A showed good solid state stability with no significant change in crystallinity and purity after being placed open for two weeks at 25° C./60% RH, 40° C./75% RH and 60° C.

Solubility

The rough solubility of crystal form A (D220-PS-01-A) of compound I in the following 21 solvents were tested at room temperature. Specifically, ~2 mg of the starting material was weighed in an HPLC vial, the solvents in the following table were added step by step (50/50/200/700 μL) until the solid is completely dissolved or the total volume reaches 1.0 mL. The obtained data is summarized in Table 1-10.

TABLE 1-10

| Rough solubility of crystal form A of compound I at room temperature | | | |
|---|---|---|---|
| Solvent | Solubility (mg/mL) | Solvent | Solubility (mg/mL) |
| DMSO | S > 40.4 | EtOAc | S < 2.1 |
| DMF | S > 41.2 | DCM | S < 2.1 |
| THF | S > 40.4 | ACN | S < 2.1 |
| $CH_3COOH$ | S > 41.8 | $H_2O$ | S < 2.1 |
| 2-MeTHF | 6.9 < S < 20.7 | Toluene | S < 2.0 |
| Acetone | 6.8 < S < 20.3 | MTBE | S < 2.0 |
| 1,4-Dioxane | 6.9 < S < 20.7 | CPME | S < 2.0 |
| MeOH | 2.0 < S < 6.6 | IPAc | S < 2.0 |
| EtOH | 2.0 < S < 6.7 | n-Heptane | S < 2.0 |
| MEK | 2.0 < S < 6.6 | MIBK | S < 2.0 |
| IPA | S < 2.1 | — | — |

Crystal form A of compound I has a low solubility in water and is easily soluble in DMSO, DMF, THF, and acetic acid. Therefore, for the purification and recrystallization process of crystal form A, it is chosen to be carried out in acetic acid. Crystal form A of compound I has a moderate solubility in acetone, so beating in acetone was chosen for further purification to remove structurally similar impurities as well as related intermediates.

CONCLUSIONS

Through a series of crystal form screening experiments on compound I, a total of six crystal forms were discovered, including three anhydrous crystal forms (crystal forms A/F/G), one hydrate crystal form E, and two solvate (crystal forms B/D). The relationship between anhydrous crystal forms was investigated by maturation/heating and suspension competition, which showed that anhydrous crystal form A of compound I is most stable at room temperature (~18° C.)/60° C. The stability relationship between anhydrous crystal form A and hydrate crystal form E of compound I was studied at different water activities. The results showed that when the water activity was between 0-0.8 at room temperature, anhydrous crystal form A of compound I is more stable; when the water activity is 1.0, the hydrate crystal form E is more stable, indicating that the key water activity for anhydrous crystal form A and hydrate crystal form E of compound I is between 0.8 and 1.0. Evaluation of the hygroscopicity of anhydrous crystal form A of compound I showed that crystal form A is hardly hygroscopic, and the crystal form unchanged before and after DVS test. Meanwhile, evaluation of the solid-state stability of anhydrous crystal form A of compound I showed that there is no significant change in crystal form and purity thereof after two weeks of open placement at 25° C./60% RH, 40° C./75% RH, and 60° C., demonstrating good solid-state stability.

Crystal forms F and G were not obtained from solution method. Crystal form F transformed into hydrate crystal form E after being placed at room temperature (18-20° C., 45%~75% RH) for 3 days, indicating unstable at room temperature. After melting, crystal form G can be recrystallized and transformed into crystal form A. The suspension competition between crystal forms A and G showed that crystal form G transformed into crystal form A in both ACN and EtOAc at room temperature and 60° C., suggesting that crystal form A is thermodynamically more stable than crystal form G.

Figure 30:
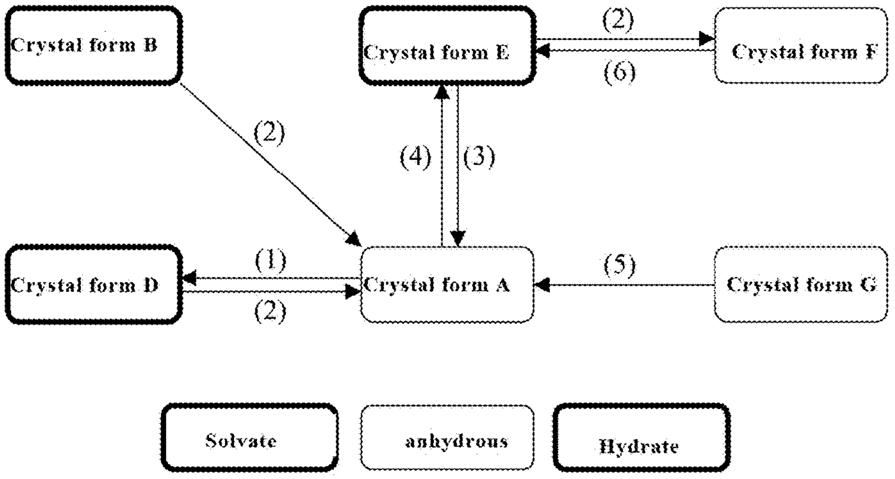
FIG. 30 shows the transformation relationship diagrams for the six crystal forms of the compound of formula I.

For the mutually transformational relationship between each crystal form, please refer to FIG. 30, and the description of the conditions were shown in Table 1-11.

TABLE 1-11

| No. | Description | No. | Description |
|---|---|---|---|
| (1) | Beating at room temperature/gas-solid diffusion in $CH_3COOH$ | (2) | dehydration/solvent |
| (3) | Beating at room temperature, water activity being 0-0.8 | (4) | Beating at room temperature, water activity being 1.0 |
| (5) | Beating at room temperature/60° C.; recrystallization after melting | (6) | Placed at room temperature for 3 days, (18~20° C., 45%~75% RH) |

All documents mentioned in the present invention are cited as references in this application, just as each document is individually cited as a reference. In addition, it should be understood that, after reading the above teaching content of the present invention, those skilled in the art can make various changes or modifications to the present invention, and these equivalent forms also fall within the scope defined by the appended claims of the present application.

The invention claimed is:

1. A crystal form of a compound of formula I:

Formula I

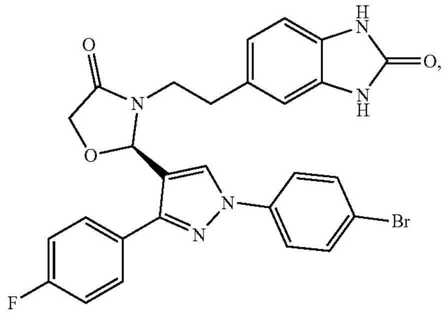

selected from the group consisting of:

i) crystal form A, wherein the X-ray powder diffraction (XRPD) pattern of crystal form A, expressed as ±0.2° 2θ, has 6 or more peaks selected from the group consisting of: 11.764±0.2° 2θ, 12.414±0.2° 2θ, 14.924±0.2° 2θ, 16.423±0.2° 2θ, 17.352±0.2° 2θ, 17.967±0.2° 2θ, 18.269±0.2° 2θ, 19.160±0.2° 2θ, 22.670±0.2° 2θ, 24.052±0.2° 2θ, 24.399±0.2° 2θ, 26.578±0.2° 2θ and 32.318±0.2° 2θ;

ii) crystal form B, wherein the XRPD pattern of crystal form B, expressed as ±0.2° 2θ, has 6 or more peaks selected from the group consisting of: 4.645±0.2° 2θ, 8.812±0.2° 2θ, 10.066±0.2° 2θ, 15.861±0.2° 2θ, 17.109±0.2° 2θ, 18.738±0.2° 2θ, 23.947±0.2° 2θ and 32.151±0.2° 2θ;

iii) crystal form D, wherein the XRPD pattern of crystal form D, expressed as ±0.2° 2θ, has 6 or more peaks selected from the group consisting of: 13.234±0.2° 2θ, 13.446±0.2° 2θ, 16.018±0.2° 2θ, 17.783±0.2° 2θ, 19.383±0.2° 2θ, 20.400±0.2° 2θ, 21.737±0.2° 2θ, 24.324±0.2° 2θ, 26.505±0.2° 2θ and 27.214±0.2° 2θ;

iv) crystal form E, wherein the XRPD pattern of crystal form E, expressed as ±0.2° 2θ, has 6 or more peaks selected from the group consisting of: 9.132±0.2° 2θ, 10.002±0.2° 2θ, 11.745±0.2° 2θ, 12.538±0.2° 2θ, 16.607±0.2° 2θ, 18.287±0.2° 2θ, 18.969±0.2° 2θ, 20.115±0.2° 2θ, 23.626±0.2° 2θ, 24.022±0.2° 2θ, 25.243±0.2° 2θ and 28.238±0.2° 2θ;

v) crystal form F, wherein the XRPD pattern of crystal form F, expressed as ±0.2° 2θ, has 6 or more peaks selected from the group consisting of: 9.246±0.2° 2θ, 10.153±0.2° 2θ, 10.749±0.2° 2θ, 11.228±0.2° 2θ, 11.851±0.2° 2θ, 12.692±0.2° 2θ, 16.050±0.2° 2θ, 16.737±0.2° 2θ, 17.255±0.2° 2θ, 18.503±0.2° 2θ, 19.210±0.2° 2θ, 20.331±0.2° 2θ, 20.687±0.2° 2θ, 21.753±0.2° 2θ and 22.536±0.2° 2θ; and vi) crystal form G, wherein the XRPD pattern of crystal form G, expressed as ±0.2° 2θ, has 6 or more peaks selected from the group consisting of: 12.411±0.2.2θ, 14.045±0.2° 2θ, 15.905±0.2° 2θ, 18.452±0.2° 2θ, 18.872±0.2° 2θ, 20.186±0.2° 2θ, 20.847±0.2° 2θ, 22.004±0.2° 2θ, 23.682±0.2° 2θ, 23.922±0.2° 2θ, 24.202±0.2° 2θ, 26.664±0.2° 2θ, 28.137±0.2° 2θ, 29.075±0.2° 2θ, 30.333±0.2° 2θ and 32.077±0.2° 2θ.

2. The crystal form according to claim 1, wherein crystal form A has 10 or more peaks selected from the group consisting of: 11.764±0.2.2θ, 12.414±0.2° 2θ, 14.924±0.2° 2θ, 16.423±0.2° 2θ, 17.352±0.2° 2θ, 17.967±0.2° 2θ, 18.269±0.2° 2θ, 19.160±0.2° 2θ, 22.670±0.2° 2θ, 24.052±0.2° 2θ, 24.399±0.2° 2θ, 26.578±0.2° 2θ and 32.318±0.2° 2θ.

3. The crystal form according to claim 1, wherein crystal form B has 7 or more peaks selected from the group consisting of: 4.645±0.2° 2θ, 8.812±0.2° 2θ, 10.066±0.2° 2θ, 15.861±0.2° 2θ, 17.109±0.2.2θ, 18.738±0.2° 2θ, 23.947±0.2° 2θ and 32.151±0.2° 2θ.

4. The crystal form according to claim 1, wherein crystal form D has 9 or more peaks selected from the group consisting of: 13.234±0.2.2θ, 13.446±0.2° 2θ, 16.018±0.2° 2θ, 17.783±0.2° 2θ, 19.383±0.2° 2θ, 20.400±0.2° 2θ, 21.737±0.2° 2θ, 24.324±0.2° 2θ, 26.505±0.2° 2θ and 27.214±0.2° 2θ.

5. The crystal form according to claim 1, wherein crystal form E has 10 or more peaks selected from the group consisting of: 9.132±0.2° 2θ, 10.002±0.2° 2θ, 11.745±0.2° 2θ, 12.538±0.2° 2θ, 16.607±0.2° 2θ, 18.287±0.2.2θ, 18.969±0.2° 2θ, 20.115±0.2° 2θ, 23.626±0.2° 2θ, 24.022±0.2° 2θ, 25.243±0.2° 2θ and 28.238±0.2° 2θ.

6. The crystal form according to claim 1, wherein crystal form F has 10 or more peaks selected from the group consisting of: 9.246±0.2.2θ, 10.153±0.2.2θ, 10.749±0.2° 2θ, 11.228±0.2° 2θ, 11.851±0.2° 2θ, 12.692±0.2° 2θ, 16.050±0.2° 2θ, 16.737±0.2° 2θ, 17.255±0.2° 2θ, 18.503±0.2° 2θ, 19.210±0.2° 2θ, 20.331±0.2° 2θ, 20.687±0.2° 2θ, 21.753±0.2° 2θ and 22.536±0.2° 2θ.

7. The crystal form according to claim 1, wherein crystal form G has 10 or more peaks selected from the group consisting of: 12.411±0.2° 2θ, 14.045±0.2° 2θ, 15.905±0.2° 2θ, 18.452±0.2° 2θ, 18.872±0.2° 2θ, 20.186±0.2° 2θ, 20.847±0.2° 2θ, 22.004±0.2° 2θ, 23.682±0.2° 2θ, 23.922±0.2° 2θ, 24.202±0.2° 2θ, 26.664±0.2.2θ, 28.137±0.2° 2θ, 29.075±0.2° 2θ, 30.333±0.2° 2θ and 32.077±0.2° 2θ.

8. A pharmaceutical composition comprising one or more crystal forms according to claim 1 and one or more pharmaceutically acceptable carriers or excipients.

9. A method of treating hepatitis B virus infection in a subject in need thereof, comprising administering to the subject, a pharmaceutical composition according to claim 8.

10. The method of claim 9, wherein the subject is a mammal.

* * * * *